United States Patent
Chen et al.

(10) Patent No.: US 12,049,463 B2
(45) Date of Patent: Jul. 30, 2024

(54) CRYSTALLINE FORM OF TOLEBRUTINIB

(71) Applicant: GENZYME CORPORATION, Cambridge, MA (US)

(72) Inventors: Minhua Chen, Suzhou (CN); Jiaming Shi, Suzhou (CN)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/818,846

(22) Filed: Aug. 10, 2022

(65) Prior Publication Data

US 2022/0389011 A1 Dec. 8, 2022

Related U.S. Application Data

(63) Continuation of application No. PCT/CN2021/132028, filed on Nov. 22, 2021.

(30) Foreign Application Priority Data

Dec. 10, 2020 (CN) .......................... 202011455573.5

(51) Int. Cl.
| | | |
|---|---|---|
| C07D 471/04 | (2006.01) | |
| A61P 25/00 | (2006.01) | |
| A61P 37/06 | (2006.01) | |

(52) U.S. Cl.
CPC ............ *C07D 471/04* (2013.01); *A61P 25/00* (2018.01); *A61P 37/06* (2018.01); *C07B 2200/13* (2013.01)

(58) Field of Classification Search
CPC ........ C07D 471/04; A61P 25/00; A61P 37/06; A61P 35/00; A61P 35/02; A61P 37/00; C07B 2200/13; A61K 31/437; A61K 31/4545
See application file for complete search history.

(56) References Cited

U.S. PATENT DOCUMENTS

| | | | |
|---|---|---|---|
| 3,760,984 | A | 9/1973 | Theeuwes |
| 3,952,741 | A | 4/1976 | Baker |
| 8,557,803 | B2 | 10/2013 | Yamamoto et al. |
| 9,199,997 | B2 | 12/2015 | Yamamoto et al. |
| 9,688,676 | B2 | 6/2017 | Owens |
| 2006/0045822 | A1 | 3/2006 | Timmons et al. |
| 2013/0079327 | A1 | 3/2013 | Yamamoto et al. |
| 2013/0197014 | A1 | 8/2013 | Chen et al. |
| 2014/0142099 | A1 | 5/2014 | Owens |
| 2014/0179680 | A1 | 6/2014 | Christopher et al. |
| 2021/0113568 | A1 | 4/2021 | Ariza |
| 2021/0244720 | A1 | 8/2021 | Cho et al. |
| 2022/0389011 | A1 | 12/2022 | Chen et al. |
| 2022/0395492 | A1* | 12/2022 | Li .......................... A61P 1/04 |

FOREIGN PATENT DOCUMENTS

| | | |
|---|---|---|
| AU | 2022290946 A1 | 1/2024 |
| CN | 103502249 A | 1/2014 |
| CN | 104640861 A | 5/2015 |
| CN | 105753863 | 7/2016 |
| EP | 2578585 A1 | 4/2013 |
| EP | 2786996 A1 | 10/2014 |
| EP | 4328226 A1 | 2/2024 |
| JP | 2010504324 A | 2/2010 |
| WO | 2003037890 A2 | 5/2003 |
| WO | 2006031878 A2 | 3/2006 |
| WO | 2006086634 A2 | 8/2006 |
| WO | 2007142755 A2 | 12/2007 |
| WO | 2008039218 A2 | 4/2008 |
| WO | 2009010491 A1 | 1/2009 |
| WO | 2010034796 A1 | 4/2010 |

(Continued)

OTHER PUBLICATIONS

English Translation of WO 2022/223027. Published Oct. 27, 2022. Retrieved from Espacenet on Jan. 23, 2023. https://worldwide.espacenet.com/patent/search/family/083723725/publication/WO2022223027A1?q=wo2022223027. (Year: 2022).*
Brittain, Harry. Polymorphism in Pharmaceutical Solids, 2nd Edition. CRC Press, Published 2009. (Year: 20).*
Dahl et al., "Radiosynthesis of a Bruton's tyrosine kinase inhibitor, [$^{11}$C]Tolebrutinib, via palladium-NiXantphos-mediated carbonylation" *J Label Compd Radiopharm*. 2020; 63:482-487.
International Search Report and Written Opinion issued in Corresponding PCT Application No. PCT/CN2021/132028, dated Feb. 18, 2022 (English Translation provided).
Core Study Information and Informed Consent Form for Clinical Trial Identifier No. DRI15928, marked "Property of the Sanofi Group—strictly confidential" and dated Oct. 22, 2018.

(Continued)

*Primary Examiner* — Amy C Bonaparte
*Assistant Examiner* — Lauren Wells
(74) *Attorney, Agent, or Firm* — McNeill Baur PLLC

(57) ABSTRACT

The present disclosure relates to a novel crystalline form of Tolebrutinib (hereinafter referred to as "Compound I") and preparation methods thereof, pharmaceutical compositions containing the crystalline form, and uses of the crystalline form for preparing BTK inhibitor drugs and drugs for treating multiple sclerosis.

4 Claims, 6 Drawing Sheets

Compound I

(56) References Cited

FOREIGN PATENT DOCUMENTS

| | | | |
|---|---|---|---|
| WO | 2011046964 A2 | 4/2011 | |
| WO | 2011152351 A1 | 12/2011 | |
| WO | 2012158764 A1 | 11/2012 | |
| WO | 2012158785 A1 | 11/2012 | |
| WO | 2012170976 A2 | 12/2012 | |
| WO | 2013116382 A1 | 8/2013 | |
| WO | 2013191965 A1 | 12/2013 | |
| WO | 2014039899 A1 | 3/2014 | |
| WO | 2014078578 A1 | 5/2014 | |
| WO | 2014100620 A2 | 6/2014 | |
| WO | 2015132799 A2 | 9/2015 | |
| WO | 2016057500 A1 | 4/2016 | |
| WO | 2016089722 A1 | 6/2016 | |
| WO | WO 2016/196840 | 12/2016 | |
| WO | WO-2016196840 A1 * | 12/2016 | ........... A61K 31/437 |
| WO | WO 2017/041536 | 3/2017 | |
| WO | 2017066014 A1 | 4/2017 | |
| WO | 2017087445 A1 | 5/2017 | |
| WO | WO 2021/150476 | 7/2021 | |
| WO | 2021247748 A1 | 12/2021 | |
| WO | 2022081512 A1 | 4/2022 | |
| WO | 2022121670 A1 | 6/2022 | |
| WO | 2022140511 A1 | 6/2022 | |
| WO | WO-2022223027 A1 * | 10/2022 | |
| WO | 2022242740 A1 | 11/2022 | |
| WO | 2022257845 A1 | 12/2022 | |
| WO | 2023031840 A1 | 3/2023 | |
| WO | 2023122072 A1 | 6/2023 | |
| WO | 2023220370 A1 | 11/2023 | |
| WO | 2023249980 A1 | 12/2023 | |
| WO | 2024006406 A1 | 1/2024 | |

OTHER PUBLICATIONS

Core Study Information and Informed Consent Form for Clinical Trial Identifier No. DRI15928, marked "Property of the Sanofi Group—strictly confidential" and dated Feb. 12, 2019.
American Cancer Society. Can Non-Hodgkins Lymphoma Be Prevented? (2016) Web: https://www.cancer.org/cancer/non-hodgkin-lymphoma/causes-risks-prevention/prevention.html.
Arora, et al., "Role of Tyrosine Kinase Inhibitors in Cancer Therapy," J. Pharmacol. Exp. Ther., 2005, 315:971-979.
Auto-immune Diseases: Medlineplus {2014). Web: http://www.nlm.nih.gov/medlineplus/autoimmunediseases.html.
Bornkamp B, et al., Package 'DoseFinding', Jan. 4, 2018.
Burger J A, et al., "Targeting B cell receptor signalling in cancer: preclinical and clinical advances.", Nat Rev Cancer. 2018;18(3):148-67.
Certified English translation of CN 105753863 A, published Jul. 13, 2016 [57 pages].
Fischer J S, et al., "The Multiple Sclerosis Functional Composite Measure (MSFC): an integrated approach to MS clinical outcome assessment. National MS Society Clinical Outcomes Assessment Task Force.", Mult Scler. 1999;5(4):244-50.
Francesco M R et.al, "PRN2246, a potent and selective blood brain barrier penetrating BTK inhibitor, exhibits efficacy in central nervous system immunity", Database accession No. EMB-619358129abstract & Multiple Sclerosis Journal 20171001 Sage Publications LTD NLD, vol. 23, No. 3, Supplement 1, Oct. 1, 2017 (Oct. 1, 2017), pp. 511; CONF Oct. 25, 2017 to Oct. 28, 2017 Paris-7th Joint.
Hauser S L, et al., "Opera I and Opera II Clinical Investigators. Ocrelizumab versus Interferon Beta-1a in Relapsing Multiple Sclerosis.", N Engl J Med. 2017;376(3):221-34.
Hemmer B, et al., "Immunopathogenesis and immunotherapy of multiple sclerosis.", Nat Clin Pract Neurol. 2006;2(4):201-11.
Hemmer B, et al., "Role of the innate and adaptive immune responses in the course of multiple sclerosis.", Lancet Neurol. 2015;14(4):406-19.
International Search Report and Written Opinion in corresponding International Patent Application No. PCT/US2021/013883, mailed Apr. 28, 2021 (12 pages).
Kappos L, et al., "Siponimod versus placebo in secondary progressive multiple sclerosis (EXPAND): a double-blind, randomised, phase 3 study.", Lancet. 2018;391(10127):1263-73.
Kurtzke J F, "Rating neurologic impairment in multiple sclerosis: an expanded disability status scale (EDSS).", Neurology. 1983;33(11):1444-52.
Lehmann-Horn K, et al., "Deciphering the role of B cells in multiple sclerosis—towards specific targeting of pathogenic function.", Int J Mol Sci. 2017;18(10):2048.
Lublin F D, et al., "Defining the clinical course of multiple sclerosis: the 2013 revisions.", Neurology. 2014;83(3):278-86.
MedicineNet.com (2004). Web. Definition of Cancer.
Merck Press release. Merck KGaA, Darmstadt, Germany, "Announces Positive Phase IIB Results for Evobrutinib in Relapsing Multiple Sclerosis.", Mar. 7, 2018.
Montalban X, et al. "Ocrelizumab versus placebo in primary progressive multiple sclerosis", N Engl J Med. 2017;376(3):209-20.
Montalban Xavier et al., 1-37 "Placebo-Controlled Trial of an Oral BTK Inhibitor in Multiple Sclerosis", The New England Journal of Medicine, vol. 380, No. 25, Jun. 20, 2019 (2019-06-20), pp. 2406-2417,10.1056/ NEJMoa1901981 Retrieved from the Internet: URL:https://www.nejm.org/doi/pdf/10.1056/NEJMoa1901981?articleTools=true> p. 2414; figure 2 abstract.
Noêl, R et al., "Synthesis and SAR of 4-(pyrazol-3-yl)-pyridines as novel c-jun N-terminal kinase inhibitors", Bioorganic & Medicinal Chemistry Letters, vol. 21 (9), pp. 2732-2735 (2011).
Online "https://www.chemicalbook.com/Chemical ProductProperty_EN_CB6195326.htm" dated by google to Oct. 1, 2014, Accessed Jun. 18, 2020. 2-Fluoroacryllic Acid.
Patani, G., Bioisosterism: A Rational Approach in Drug Design. Chem. Rev. 1996, vol. 96, No. 8, pp. 3147-3176.
Pennington et al., "The Necessary Nitrogen Atom: A Versatile High-Impact Design Element for Multiparameter Optimization," J. Med. Chem., ePub Feb. 8, 2017, 28 pages, DOI: 10.1021/acs.jmedchem 6b01807.
Press Release: "Sanofi to acquire Principia Biopharma", 6 pages (Aug. 17, 2020).
Rahmanzadeh R, et al., "Multiple sclerosis pathogenesis: missing pieces of an old puzzle.", Rev Neurosci. Jun. 8, 2018. pii: /j/revneuro.ahead-ofprint/revneuro-2018-0002/revneuro-2018-0002.XML. doi: 10.1515/revneuro-2018-0002.
Wakefield, Basil "Fluorinated Pharmaceuticals" Innovations in Pharmaceutical Technology 2003, 74, 76-78.
WebMD. 10 Ways to Prevent Psoriasis Flare-Ups. (2016) Web< http://www.webmd.com/skin-problems-and-treatments/psoriasis/prevent-flare-ups>.
WebMD. Multiple Sclerosis (MS)-Prevention. (2015) Web: < http://wwwv.webmd.com/multiple-sclerosis/tc/multiple-sclerosis-ms-prevention>.
Wermuth, C. G., "Molecular Variation Based on Isosteric Replacements", in Chapter 13, The Practice of Medicinal Chemistry, Academic, pp. 203-237 (1996).
Kalincik et al., "Treatment effectiveness of alemtuzumab compared with natalizumab, fingolimod, and interferon beta in relapsing-remitting multiple sclerosis: a cohort study", Lancet Neurol, 16, pp. 271-281 (2017).
Kaminski, "Treatment of Myasthenia Gravis. In: Kaminski HJ, Kusner LL, editors", Current Clinical Neurology: Myasthenia Gravis and Related Disorders 3rd edition, pp. 169-187 (2018).
Kapoor et al., "Effect of natalizumab on disease progression in secondary progressive multiple sclerosis (ASCEND): a phase 3, randomised, double-blind, placebo-controlled trial with an open-label extension", Lancet Neurol, 17: 405-415 (2018).
Kappos et al., "Ocrelizumab in relapsing-remitting multiple sclerosis: a phase 2, randomised, placebo-controlled, multicentre trial", The Lancet, 378(9805), pp. 1779-1787 (Nov. 19, 2011).
Kappos, L., et al., "Natalizumab treatment for multiple sclerosis: recommendations for patient selection and monitoring", Lancet Neurol, 6(5), pp. 431-441 (2007).
Kim et al., "Imidazo[1,5-a]quinoxalines as irreversible BTK inhibitors for the treatment of rheumatoid arthritis", Bioorg Med Chem Lett., 21, pp. 6258-6263 (2011).

(56) References Cited

OTHER PUBLICATIONS

Kozuki, T., "Skin problems and EGFR-tyrosine kinase inhibitor." Jpn J Clin Oncol., 46(4), pp. 291-298. (Apr. 2016).
Krupp et al., "International Pediatric Multiple Sclerosis Study Group. International Pediatric Multiple Sclerosis Study Group", Multiple Sclerosis Journal., 19, pp. 1261-1267 (2011).
Kuks J.B.M., "Clinical Presentations of Myasthenia Gravis: Myasthenia Gravis and Related Disorders", Current Clinical Neurology, 2018. p. 58-100.
Langer-Gould et al., "Incidence of acquired CNS demyelinating syndromes in a multiethnic cohort of children", Neurology, 77(12), pp. 1143-1148 (2011).
Lazaridis et al., "Myasthenia Gravis: Autoantibody Specificities and Their Role in MG Management", Front Neurol, p. 30;11:59698 (2020).
Lebakken et al., "Development and applications of a broad-coverage, TR-FRET-based kinase binding assay platform", J Biomol Screen, 14, pp. 924-935 (2009).
Lee et al., "Juvenile Myasthenia Gravis in Korea: Subgroup Analysis According to Sex and Onset Age", J Child Neurol, 31(14), pp. 1561-1568 (Dec. 2016).
Lee et al., "Safety, pharmacokinetics, and pharmacodynamics of BMS-986142, a novel reversible BTK inhibitor, in healthy participants", European Journal of Clinical Pharmacology, 73(6), pp. 689-698 (2017).
Li et al., "Comparative efficacy and acceptability of disease-modifying therapies in patients with relapsing-remitting multiple sclerosis: a systematic review and network meta-analysis", J Neurol, pp. doi: 10.1007/s00415-019-09395-w (2019).
Linder et al., "Outcome in juvenile-onset myasthenia gravis: a retrospective study with long-term follow-up of 79 patients", J Neurol., 244(8), pp. 515-520 (Aug. 1997).
Lindstrom et al., "Antibody to acetylcholine receptor in myasthenia gravis. Prevalence, clinical correlates, and diagnostic value", Neurology., 26(11), pp. 1054-1059 (Nov. 1976).
Lipsky et al., "Incidence and risk factors of bleeding-related adverse events in patients with chronic lymphocytic leukemia treated with ibrutinib", Haematologica., 100(12), pp. 1571-1578 (Dec. 2015).
Liu et al., "Analysis of mortality and related factors in 2195 adult myasthenia gravis patients in a 10-year follow-up study", Neurol India, 65(3), pp. 518-524 (May-Jun. 2017).
Liu et al., "Disability outcome measures in therapeutic trials of relapsing-remitting multiple sclerosis: effects of heterogeneity of disease course in placebo cohorts", J Neurol Neurosurg Psychiatry, vol. 68, pp. 450-457 (2000).
Liu et al., "Tacrolimus Improves Symptoms of Children With Myasthenia Gravis Refractory to Prednisone", Pediatr Neurol., 77, pp. 42-47 (Dec. 2017).
Lynch et al., "Epidermal growth factor receptor inhibitor-associated cutaneous toxicities: an evolving paradigm in clinical management", Oncologist, 12(5), pp. 610-621 (May 2007).
Mangla et al., "Pleiotropic consequences of Bruton tyrosine kinase deficiency in myeloid lineages lead to poor inflammatory responses", Blood, 104, pp. 1191-1197 (2004).
Mansukhani et al., "Incidence and Ocular Features of Pediatric Myasthenias", Am J Ophthalmol., 200, pp. 242-249 (Apr. 2019).
Marta et al., "Microglial Fc receptors mediate physiological changes resulting from antibody cross-linking of myelin oligodendrocyte glycoprotein", J Neuroimmunol., 196(1-2), pp. 35-40 (2008).
Massimiliano et al., "Smoothness of gait detects early alterations of walking in persons with multiple sclerosis without disability", Gait & Posture, 58, pp. 307-309 (2017).
McGrogan et al., "The Incidence of Myasthenia Gravis: A Systematic Literature Review", Neuroepidemiology, 34, pp. 171-183 (2010).
McPherson et al., "Correlation of Quantitative Myasthenia Gravis and Myasthenia Gravis Activities of Daily Living scales in the MGTX study", Muscle Nerve, 62(2), pp. 261-266 (2020).
Mexhitaj et al., "Abnormal effector and regulatory T cell subsets in paediatric-onset multiple sclerosis", Brain, 142(3), pp. 617-632 (2019).
Meyer-Moock et al., "Systematic literature review and validity evaluation of the expanded disability status scale (EDSS) and the multiple sclerosis functional composite (MSFC) in patients with multiple sclerosis", BMC Neurol., 14, p. 58 (Mar. 25, 2014).
Miller, R., "Chapter 10—Population Pharmacokinetics", Principles of clinical pharmacology, second edition, pp. 129-139 (2007).
Mohamed et al., "Bruton's tyrosine kinase (Btk): function, regulation, and transformation with special emphasis on the PH domain", Immunol Rev., 228, pp. 58-73 (2009).
Montalban et al., "Placebo controlled trial of an oral BTK inhibitor in multiple sclerosis", N Engl J Med., 380, pp. 2406-2417 (2019).
Morrow et al., "Predicting loss of employment over three years in multiple sclerosis: Clinically meaningful cognitive decline", Clin Neuropsychol, 24, pp. 1131-1145 (2010).
Mowry et al., "Multiple sclerosis susceptibility genes: associations with relapse severity and recovery", PLoS One 2013; 8:e75416.
Munot et al., "242nd ENMC international diagnosis and management of juvenile myasthenia gravis Hoofddorp, the Netherlands, Mar. 1-3, 2019", Neuromuscul Disord., 30, pp. 254-264 (2010).
Muppidi et al., "MG-ADL: Still a relevant outcome measure", Muscle Nerve, vol. 44, pp. 727-731 (2011).
Muppidi, "The myasthenia gravis-specific activities of daily living profile", Ann N.Y. Acad Sci, vol. 1274, pp. 114-119 (2012).
Murray et al., "Semiparametric Bayesian Commensurate Survival Model for Post-Market Medical Device Surveillance with Non-Exchangeable Historical Data", Biometrics, 70, pp. 185-191 (Mar. 2014).
Narayanaswami et al., "International Consensus Guidance for Management of Myasthenia Gravis: 2020 Update", Neurology, 96(3), pp. 114-122 (Jan. 19, 2021).
National MS Society web site (https://www.nationalmssociety.org/What-is-MS/MS-FAQ-s).
Navarro et al., "Antiviral Immunity", Curr Immunol Rev., 7, pp. 19-24 (2011).
O'Connell et al., "Management of Juvenile Myasthenia Gravis", Front. Neurol., 11, p. 743 (2020).
O'Connor et al., "Randomized Trial of Oral Teriflunomide for Relapsing Multiple Sclerosis", N Engl J Med, 365, pp. 1293-1303 (2011).
Okun et al., "Involvement of Fc receptors in disorders of the central nervous system", Neuromolecular Med., 12(2), pp. 164-178 (2010).
Otallah et al., "Pediatric Multiple Sclerosis: an Update", Curr Neurol Neurosci Rep., 18(11), p. 76 (Sep. 18, 2018).
Owens et al., "Phase 1 clinical trial evaluating safety, exposure and pharmacodynamics of BTK inhibitor tolebrutinib (PRN2246, SAR442168)", Clin Transl Sci., 00, pp. 1-9 (2021).
Parr et al., "How common is childhood myasthenia? The UK incidence and prevalence of autoimmune and congenital myasthenia", Arch Dis Child, 99(6), pp. 539-542 (Jun. 2014).
Pedersen et al., "Late-onset myasthenia not on the increase: a nationwide register study in Denmark", 1996-2009. Eur J Neurol., 20, pp. 309-314 (2013).
Peragallo Jh., "Pediatric Myasthenia Gravis", Semin Pediatr Neurol., 24(2), pp. 116-121 (May 2017).
Phillips et al., "Sustained improvement in Expanded Disability Status Scale as a new efficacy measure of neurological change in multiple sclerosis: treatment effects with natalizumab in patients with relapsing", Multiple Sclerosis Journal, 17(8), pp. 970-979 (2011).
Popperud et al., "Juvenile myasthenia gravis in Norway: HLA-DRB1_04:04 is positively associated with prepubertal onset", PLoS One, 12(10): e0186383 (2017).
Weber et al., "B cell activation influences T cell polarization and outcome of anti-CD20 B cell depletion in CNS autoimmunity", Ann Neurol., 68(3), pp. 369-383 (Sep. 2010).
Ragheb et al., "B-Cell-Activating Factor and Autoimmune Myasthenia Gravis", Autoimmune Dis., 2011; 939520.
Raisch et al., "Detection of cases of progressive multifocal leukoencephalopathy associated with new biologicals and targeted cancer therapies from the FDA's adverse event reporting system", Expert Opin Drug Saf., 15(8), pp. 1003-1011 (2016).

(56) References Cited

OTHER PUBLICATIONS

Ramanujam et al., "Utilizing twins concordance rates to infer the predisposition to myasthenia gravis", Twin Res. Hum. Genet., 13, pp. 129-136 (2011).
Rankin et al., "Selective inhibition of BTK prevents murine lupus and antibody-mediated glomerulonephritis", J Immunol., 191(9), pp. 4540-4550 (2013).
Rasche et al., "MRI Markers and Functional Performance in Patients With CIS and Ms: A Cross-Sectional Study", Front Neurol, vol. 9(718), pp. 1-12 (2018).
Reich et al. "Safety and efficacy of tolebrutinib, an oral brain-penetrant BTK inhibitor, in relapsing multiple sclerosis: a phase 2b, randomised, double-blind, placebo-controlled trial", Lancet Neurol., 20, pp. 729-738 (2021).
Renoux et al., "Natural History of Multiple Sclerosis with Childhood Onset", New England Journal of Medicine, 356, pp. 2603-2613 (2007).
Renoux et al., "The natural history of multiple sclerosis with childhood onset", Clin Neurol Neurosug., Nov. 2008; 110 (9), pp. 897-904. doi 10.1016/j.clineuro.2008.04.009. Epub Jun. 4, 2008.
Rigg et al., "Oral administration of Bruton's tyrosine kinase inhibitors impairs GPVI-mediated platelet function", Am J Physiol Cell Physiol., 310(5), pp. C373-380 (Mar. 2016).
Robinet et al., "Review on Toll-Like Receptor Activation in Myasthenia Gravis: Application to the Development of New Experimental Models", Clin Rev Allergy Immunol., 52(1), pp. 133-147 (Feb. 2017).
Wassmer et al., "International Pediatric MS Study Group Global Members Symposium report", Neurology, 87(Suppl 2): S110-S116 (2016).
Roschewski et al., "Inhibition of Burton tyrosine kinase in patients with severe COVID-19", Sci. Immunol. 10.1126/sciimmunol. abd0110 (2020).
Rovaris et al., "MRI markers of destructive pathology in multiple sclerosis-related cognitive dysfunction", Journal of the Neurological Sciences 245(1-2), pp. 111-116 (2006).
Sanders, D., et al., "International consensus guidance for management of myasthenia gravis: Executive summary", Neurology., 87(4), pp. 419-425 (Jul. 26, 2016).
Scalfari et al., "Onset of secondary progressive phase and long-term evolution of multiple sclerosis", Neurol Neurosurg Psychiatry., pp. 67-75 (2013).
Scalfari, et al., "Mortality in patients with multiple sclerosis", Neurology, 81, pp. 184-192 (2013).
Scheers et al., "Absorption, Metabolism, and Excretion of Oral 14C Radiolabeled Ibrutinib: An Open-Label, Phase 1, Single-Dose Study in Healthy Men", Drug Metab Dispos, vol. 43, pp. 289-207 (Feb. 2015).
Schutt, et al., "BTK knockout rat model demonstrates rat-specific BTK inhibitor-related pancreatic pathology is on-target and unlikely to be relevant for humans [abstract 70]", Presented at 35th Annual Symposium of the Society of Toxicologic Pathology; Jun. 26-29, 2016; San Diego, CA. p. 77.
Selcen et al., "High-dose intravenous immunoglobulin therapy in juvenile myasthenia gravis", Pediatr Neurol, 22, pp. 40-43 (2000).
Sengupta et al., "MicroRNA and mRNA expression associated with ectopic germinal centers in thymus of myasthenia gravis", PLoS One, 13(10):e0205464 (Oct. 11, 2018).
Shatzel et al., "Ibrutinib-associated bleeding: pathogenesis, management and risk reduction strategies", J Thromb Haemost., 15(5), pp. 835-847., Epub Mar. 27, 2017. (May 2017).
Sibaud et al., "Dermatological Toxicities of Bruton's Tyrosine Kinase Inhibitors", Am. J. Clin. Dermatol., 21, pp. 799-812 (2020).
Sideras et al., "Molecular and cellular aspects of X-linked agammaglobulinemia",, Adv Immunol., 59, pp. 135-223 (1995).
Sobieszczuk et al., "Myasthenia Gravis in Poland: National Healthcare Database Epidemiological Study", Neuroepidemiology, 19, pp. 1-8 (Feb. 2021).
Sormani et al., "MRI lesions as a surrogate for relapses in multiple sclerosis: a meta analysis of randomised trials", Lancet Neurol., 12(7), pp. 669-676 (Jul. 2013).
Sparaco et al., "The Role of Wearable Devices in Multiple Sclerosis", Mult Scler Int.; Review Article, v. 2018.
Sprenger et al., "Association of brain volume loss and long-term disability outcomes in patients with multiple sclerosis treated with teriflunomide", Multiple Sclerosis Journal, pp. 1-10 (2019).
Tan et al., "Targeting the SYK-BTK axis for the treatment of immunological and hematological disorders: Recent progress and therapeutic perspectives", Pharmacol Ther., 138(2), pp. 294-309 (2013).
Tang, et al., "Cardiac side effects of bruton tyrosine kinase (BTK) inhibitors", Leuk Lymphoma, 59(7), pp. 1554-1564 (Jul. 2018).
Thompson et al., "Multiple sclerosis", Lancet, 391(10130), 1622-1636 (2018).
Tomassini et al., "Predicting the profile of increasing disability in multiple sclerosis", Multiple Sclerosis Journal, 25(9), pp. 1306-1315 (2019).
Tsai et al., "Increased subsequent risk of myasthenia gravis in children with allergic diseases", J Neuroimmunol., 276 (1-2), pp. 202-206 (Nov. 15, 2014).
Tur et al., "Assessing treatment outcomes in multiple sclerosis trials and in the clinical setting", Neurology, 14, pp. 75-93 (2018).
US FDA. In vitro metabolism and transporter-mediated drug-drug interaction studies. [Online]. [Cited Nov. 20, 2018]. Available from:URL:https://www.fda.gov/downloads/Drugs/GuidanceComplianceRegulatoryInformation/Guidances/UCM581965.pdf.
Uzawa et al., "Roles of cytokines and T cells in the pathogenesis of myasthenia gravis", Clin Exp Immunol., 203, pp. 366-374 (2020).
Van Rosmalen et al., "Including historical data in the analysis of clinical trials: Is it worth the effort?", Statistical Methods in Medical Research., 27(10), pp. 3167-3182 (2018).
Vanderver et al., "Relative incidence of inherited white matter disorders in childhood to acquired pediatric demyelinating disorders", Semin Pediatr Neurol., 19(4), pp. 219-223. doi:10.1016/j.spen.2012.10.001.
Vandiedonck et al., "Genetics of autoimmune myasthenia gravis: the multifaceted contribution of the HLA complex", J Autoimmun., 25 Suppl:6-11 (2005).
Venkateswaran et al., "Pediatric Multiple Sclerosis", The Neurologist, 16(2), pp. 92-105 (Mar. 2010).
Volmering et al., "The Neutrophil Btk Signalosome Regulates Integrin Activation During Sterile Inflammation", Immunity, 44, pp. 73-87 (2016).
Von Budingen et al., "B cell exchange across the blood brain barrier in multiple sclerosis", J. Clin. Invest., 122(12), pp. 4533-4543 (Dec. 2012).
Von Lindern et al., "Control of erythropoiesis by erythropoietin and stem cell factor: A novel role for Bruton's tyrosine kinase", Cell Cycle, 3(7), pp. 876-879 (2004).
Waldman et al., "Multiple sclerosis in children: an update on clinical diagnosis, therapeutic strategies, and research", Lancet Neurol., 13(9), pp. 936-948. doi: 10.1016/S1474-4422(14)70093-6. Review (Sep. 2014).
Waldman et al., "Pediatric multiple sclerosis: Clinical features and outcome", Neurology, 87(9 Suppl 2): S74-81. (Aug. 30, 2016).
Wang, M.L., "Targeting BTK with Ibrutinib in Relapsed or Refractory Mantle-Cell Lymphoma." N Engl J Med., 369(6), Jun. 19, 2013. [Epub ahead of print].
Core Study Information and Informed Consent Form for Clinical Trial Identifier No. EFC16033, marked "Property of the Sanofi Group—strictly confidential" and dated, Jul. 6, 2023 (20 pages).
Core Study Information and Informed Consent Form for Clinical Trial Identifier No. EFC16034, marked "Property of the Sanofi Group—strictly confidential" and dated Feb. 27, 2023 (20 pages).
Core Study Information and Informed Consent Form for Clinical Trial Identifier No. EFC16035, marked "Property of the Sanofi Group—strictly confidential" and dated Feb. 27, 2023 (21 pages).
Core Study Information and Informed Consent Form for Clinical Trial Identifier No. EFC16645, marked "Property of the Sanofi Group—strictly confidential" and dated Feb. 27, 2023 (20 pages).

(56) References Cited

OTHER PUBLICATIONS

Core Study Information and Informed Consent Form for Clinical Trial Identifier No. EFC17262, marked "Property of the Sanofi Group—strictly confidential" and dated Sep. 14, 2022 (22 pages).
Core Study Information and Informed Consent Form for Clinical Trial Identifier No. LTS16004, marked "Property of the Sanofi Group—strictly confidential" and dated Jun. 28, 2023 (19 pages).
Core Study Information and Informed Consent Form for Clinical Trial Identifier No. POP16398, marked "Property of the Sanofi Group—strictly confidential" and dated Jun. 16, 2022 (22 pages).
Core Study Information and Informed Consent Form for Clinical Trial Identifier No. POP16399, marked "Property of the Sanofi Group—strictly confidential" and dated May 31, 2022 (22 pages).
Participant Information Sheet and Informed Consent Form for Sponsor Study No. BEX16018, marked "Property of the Sanofi Group—strictly confidential" and dated Aug. 9, 2019 (30 pages).
Caira, Mino R., "Crystalline Polymorphism of Organic Compounds", Topics in Current Chemistry, 198, pp. 163-208 (Jan. 1, 1998).
English Translation of Japanese Patent No. 2012246314A, issued on Dec. 13, 2012 (120 pages) (cited in SB08 on Jun. 29, 2023).
International Preliminary Report on Patentability issued in International Application No. PCT/CN2022/096779 on Nov. 21, 2023 (12 pages).
International Search Report and Written Opinion issued in International Application No. PCT/US2021/064800 on Apr. 4, 2022 (10 pages).
International Search Report and Written Opinion issued in International Application No. PCT/US2022/053479 on Apr. 11, 2023 (13 pages).
International Search Report and Written Opinion issued in International Application No. PCT/US2023/022042 on Aug. 11, 2023 (13 pages).
International Search Report and Written Opinion issued in International Application No. PCT/US2023/025808 on Oct. 2, 2023 (24 pages).
International Search Report and Written Opinion issued in International Application No. PCT/US2023/026526 on Oct. 12, 2023 (12 pages).
International Search Report and Written Opinion issued in International Application No. PCT/US2023/034655 on Feb. 2, 2024 (13 pages).
International Search Report and Written Opinion issued in International Application No. PCT/US2023/084784 on Mar. 18, 2024 (17 pages).
International Search Report and Written Opinion mailed Aug. 16, 2016, issued in corresponding International Application No. PCT/US2016/035588 (10 pages).
Lee et al., "B cell depletion therapies in autoimmune disease: advances and mechanistic insights", Nature Reviews Drug Discovery, 20(3), pp. 179-199 (Dec. 15, 2020).
Mader et al., "Pathomechanisms in demyelination and astrocytopathy: autoantibodies to AQP4, MOG, GFAP, GRP78 and beyond", Current Opinion in Neurology, 35(3), pp. 427-435 (Jun. 1, 2022).
Mehta et al., "Iron is a Sensitive Biomarker for Inflammation in Multiple Sclerosis Lesions", PLOS ONE, 8(3), p. e57573 (Mar. 14, 2013).
Oh et al., "Emerging therapies to target CNS pathophysiology in multiple sclerosis", Nature Review Neurology, 18(8), pp. 466-475 (Jun. 13, 2022).
Oh et al., "Safety and clinical outcomes from the long-term extension study of tolebrutinib in patients with relapsing Multiple Sclerosis: 18-month results", Neurology, 98(18S), pp. 20220424-20220426 (May 3, 2022).
Panichi Zanin Ferreira et al., "Disease progression and oxidative stress are associated with higher serum ferritin levels in patients with multiple sclerosis", J Neurol Sci, 373, pp. 236-241 (Epub Dec. 27, 2016).

Pellerin et al., "MOG autoantibodies trigger a tightly-controlled FcR and BTK-drive microglia proliferative response", BRAIN, 144(8), pp. 2361-2374 (Sep. 4, 2021).
Rudko et al., "Monitoring increased iron levels in multiple sclerosis using MRI", Future Neurology, 9(4), pp. 387-391 (Jul. 1, 2014).
Sfagos et al., "Serum ferritin, transferrin and soluble transferrin receptor levels in multiple sclerosis patients", Multiple Sclerosis Journal, 11(3), pp. 272-275 (Jun. 1, 2005).
Stathopoulos et al., "Evolution of Anti-B Cell Therapeutics in Autoimmune Neurological Diseases", Neurotherapeutics, 19(3), pp. 691-710 (Feb. 18, 2022).
Torke et al., "Inhibition of Bruton's tyrosine kinase interfers with pathogenic B-cell development in inflammatory CNS demyelinating disease", ACTA Neuropathologica, 140(4), pp. 535-548 (Aug. 6, 2020).
Traboulsee et al., "Lack of rebound disease activity in patients with relapsing multiple sclerosis following placebo run-out in the tolebrutinib phase 2b trial", Multiple Sclerosis Journal, 28(3_suppl), pp. 130-691 (Oct. 12, 2022).
Wong et al., "Real-world validation of the 2017 McDonald criteria for pediatric MS", Neurol, 6:e528 (2019).
Wu et al., "Second-generation inhibitors of Bruton tyrosine kinase", J Hematol Oncol., 9(1), p. 80 (2016).
Xu et al., "RN486, a selective Bruton's tyrosine kinase inhibitor, abrogates immune hypersensitivity responses and arthritis in rodents", J Pharmacol Exp Ther, 341(1), pp. 90-103 (2012).
Yan et al., "Comparison of anti-acetylcholine receptor profiles between Chinese cases of adult-and juvenile-onset myasthenia gravis using cell-based assays", J Neuroimmunol., 349:577403 (Dec. 15, 2020).
Yeh et al., "Pediatric multiple sclerosis", Nat. Rev. Neurol., 5, pp. 621-631 (2009).
Yeshokumar et al., "Pediatric multiple sclerosis", Curr Opin Neurol., 30(3), pp. 216-221 (Jun. 2017).
Yi et al., "B cells in the pathophysiology of myasthenia gravis", Muscle Nerve, 57(2), pp. 172-184 (Feb. 2018).
Zhao, et al., "The role of innate immunity in myasthenia gravis", Autoimmun Rev, 20(5):102800 (2021).
Zhong et al., "HLA in myasthenia gravis: From superficial correlation to underlying mechanism", Autoimmun Rev., 18 (9):102349 (Sep. 2019).
Acalabrutinib [prescribing information]. Wilmington, DE: AstraZeneca Pharmaceuticals LP;2017 [Revised Oct. 2017; cited Aug. 12, 2021]. Available from:https://www.accessdata.fda.gov/drugsatfda_docs/label/2017/210259s000lbl.pdf.
Advani, et al., "Bruton tyrosine kinase inhibitor ibrutinib (PCI-32765) has significant activity in patients with relapsed/refractory B-cell malignancies." Journal of Clinical Oncology, 31, pp. 88-94 (2013).
Aguilar, C, "Ibrutinib-related bleeding: pathogenesis, clinical implications and management." Blood Coagul Fibrinolysis, 29(6), pp. 481-487 (Sep. 2018).
Alabbad, et al. "Monoclonal Antibody Based Therapies for Myasthenia Gravis." BioDrugs., 34(5), pp. 557-566 (Oct. 2020).
Alroughani et al., "Pediatric multiple sclerosis—a review", BMC Neurology, 18:27 (2018) (8 pages).
Amato et al., "Interrater reliability in assessing functional systems and disability on the Kurtzke scale in multiple sclerosis", Arch Neurol., 45(7), pp. 746-748 (Jul. 1988).
Aragones et al., "Prevalence of myasthenia gravis in the Catalan county of Osona", Neurologia., 32(1), pp. 1-5 (Jan.-Feb. 2017).
Azevedo et al., "Whole-brain atrophy: ready for implementation into clinical decision-making in multiple sclerosis?", Curr Opin Neurol., 29(3), pp. 237-242 (Jun. 2016).
Balto et al., "Accuracy and precision of smartphone applications and commercially available motion sensors in multiple sclerosis", Mult Scler J Exp Transl Clin (Mar. 4, 2016).
Banwell et al., "Incidence of acquired demyelination of the CNS in Canadian children", Neurology, 72(3), pp. 232-239 (Jan. 20, 2009). doi: 10.1212/01.wnl.0000339482. 84392.bd.
Banwell et al., "Multiple sclerosis in children: clinical diagnosis, therapeutic strategies, and future directions", Lancet Neurology, 6, pp. 887-902 (2007).

(56) References Cited

OTHER PUBLICATIONS

Barnett et al., "Measuring Clinical Treatment Response in Myasthenia Gravis", Neurol Clin, 36(2), pp. 339-353 (2018).
Barnett et al., "A conceptual framework for evaluating impairments in myasthenia gravis", PLoS One, 9(5), pp. 1-9 (2014).
Barnett et al., "Development and validation of the Myasthenia Gravis Impairment Index", Neurology, 87(9), pp. 879-886 (Aug. 30, 2016).
Barnett et al., "Myasthenia Gravis Impairment Index: Responsiveness, meaningful, change, and relative efficiency", Neurology, 5:89(23), pp. 2357-2364 (2017).
Barohn et al., "Reliability testing of the quantitative myasthenia gravis score", Ann N.Y. Acad Sci, 841, pp. 769-772 (1998).
Bar-Or et al., Clinical Perspectives on the Molecular and Pharmacological Attributes of Anti-CD20 Therapies for Multiple Sclerosis, CNS Drugs, 35(9), pp. 985-997 (Sep. 2021).
Barraude et al., "Clinical features and evolution of juvenile myasthenia gravis in a French cohort", Muscle Nerve, 57(4), pp. 603-609 (Apr. 2018).
Bedlack et al., "Quantitative myasthenia gravis score: Assessment of responsiveness and longitudinal validity", Neurology, vol. 64, pp. 1968-1970 (2005).
Benedict et al., "Characterizing cognitive function during relapse in multiple sclerosis", Mult Scler., 20(13), pp. 1745-1752 (Nov. 2014) doi: 10.1177/1352458514533229.
Benedict et al., "Improved cognitive outcomes in patients with relapsing-remitting multiple sclerosis treated with daclizumab beta: results from the Decide study", Mult Scler J, 24(6), pp. 795-804 (2018).
Berger, et al., "PML diagnostic criteria: consensus statement from the AAN Neuroinfectious Disease Section", Neurology, vol. 80, No. 15, pp. 1430-1438 (Apr. 9, 2013).
Bergsland et al., "Subcortical and Cortical Gray Matter Atrophy in a Large Sample of Patients with Clinically Isolated Syndrome and Early Relapsing-Remitting Multiple Sclerosis", Am J Neuroradiol, 33(8), pp. 1573-1578 (2012).
Berrih-Aknin, et al., "Immunopathogenesis of Myasthenia Gravis: a comprehensive review of immune dysregulation and etiological mechanisms", J Autoimmun., vol. 52, pp. 90-100 (Aug. 2014).
Bhaskaran, et al., "Pancreatic Effects of a Bruton's Tyrosine Kinase Small-molecule Inhibitor in Rats Are Strain-dependent", Toxicol Pathol., vol. 46(4), pp. 460-472 (Jun. 2018).
Dilokthornsakul et al., "Multiple Sclerosis Prevalence in the United States Commercially Insured Population", Neurology, 86(11), pp. 1014-1021 (Mar. 15, 2016).
Blauth, et al., "The ins and outs of B cells in multiple sclerosis", Front. Immunol., vol. 6, p. 565 (Nov. 5, 2015).
Boiko et al., "Early onset multiple sclerosis: a longitudinal study", Neurology, 59, pp. 1006-1010 (2002).
Breiner et al., "Epidemiology of myasthenia gravis in Ontario, Canada", Neuromuscul Disord., 26(1), pp. 41-46 (Jan. 2016).
Brenneman et al., "Mechanistic investigations of test article-induced pancreatic toxicity at the endocrine-exocrine interface in the rat", Toxicol Pathol., 42(1), pp. 229-242 (Jan. 2014).
Brown et al. "Incidence of and risk factors for major haemorrhage in patients treated with ibrutinib: An integrated analysis.", Br. J. Haematol., 184(4), pp. 558-569 ( Feb. 2019).
Bubuioc et al. "The epidemiology of myasthenia gravis.", J Med Life., 14(1), pp. 7-16 (Jan.-Mar 2021).
Buoen, C., et al. "How first-time-in-human studies are being performed: a survey of phase I dose-escalation trials in healthy volunteers published between 1995 and 2004." J Clin Pharmacol. Oct. 2005, vol. 45, No. 10, pp. 1123-1136.
Burdick et al., "Confidence intervals on variance components.", Marcel Dekker, NY. 1992.
Bye et al., "Severe platelet dysfunction in NHL patients receiving ibrutinib is absent in patients receiving acalabrutinib", Blood Adv., 1(26), pp. 2610-2623 (Dec. 12, 2017).
Byrd et al., "Acalabrutinib (ACP-196) in relapsed chronic lymphocytic leukemia", N Engl J Med., 374(4), pp. 323-332 (2016).
Byrd et al., "Targeting BTK with Ibrutinib in Relapsed Chronic Lymphocytic Leukemia", N Engl J Med., 369(1), pp. 32-42 (Jun. 19, 2013).
Cadavid et al., "The EDSS-Plus, an improved endpoint for disability progression in secondary progressive multiple sclerosis", Multiple Sclerosis Journal, 23(1), pp. 94-105 (2017).
Carr et al., "A systematic review of population based epidemiological studies in Myasthenia Gravis", BMC Neurology, 10(46), pp. 1-9 (Jun. 18, 2010).
Case et al., "Accuracy of smartphone applications and wearable devices for tracking physical activity data", JAMA, 313(6), pp. 625-626 (Feb. 10, 2015).
Cavalcante et al., "Etiology of myasthenia gravis: innate immunity signature in pathological thymus", Autoimmun Rev., 12(9), pp. 863-874 (Jul. 2013).
Cavalcante et al., "Toll-like receptors 7 and 9 in myasthenia gravis thymus: amplifiers of autoimmunity?" Annals of the New York Academy of Science, Feb. 2018;1413(1):11-24.
Center for Drug Evaluation and Research, Summary Basis of Approval, Acalabrutinib, Application No. 210259Orig1s000, 2017.
Center for Drug Evaluation and Research, Summary Basis of Approval, Ibrutinib, Application No. 205552Orig1s000, 2013.
Chang, Betty Y., et al., "The Bruton tyrosine kinase inhibitor PCI-32765 ameliorates autoimmune arthritis by inhibition of multiple effector cells." Arthritis Research & Therapy, 2011; vol. 13, Article No. R115.
Chen et al., "A 2-in-1 Adaptive Phase 2/3 Design for Expedited Oncology Drug Development", Contemporary Clinical Trials, vol. 64, pp. 238-242.
Chen et al., "The effect of Bruton's tyrosine kinase (BTK) inhibitors on collagen-induced platelet aggregation, BTK, and tyrosine kinase expressed in hepatocellular carcinoma (TEC)", Eur J Haematol., 2018;101, pp. 604-612.
Chiang et al., "Juvenile myasthenia gravis", Muscle Nerve, 39, pp. 423-431 (2009).
Chisari et al., "Rituximab for the treatment of multiple sclerosis: a review", J Neurol., 8, pp. 1-25 (2022).
Chitnis et al., "Demographics of pediatric-onset multiple sclerosis in an MS center population from the Northeastern United States", Mult Scler., 15(5), pp. 627-631 (May 2009) doi: 10.1177/1352458508101933. Epub Mar. 19, 2009.
Clinical Trial Results of EU Clinical Trials Register No. 2018-003927-12, "A Phase2b dose-finding study for SAR442168, a Bruton's tyrosine kinase inhibitor, in participants with relapsing multiple sclerosis", Dec. 31, 2020 (23 pages).
ClinicalTrial.gov ID No. NCT05132569, "Efficacy and Safety of Tolebrutinib (SAR442168) Tablets in Adult Participants With Generalized Myasthenia Gravis (URSA)", Last Updated Mar. 10, 2023 (9 pages).
ClinicalTrials.gov ID No. NCT03889639, "Dose-finding Study for SAR442168 in Relapsing Multiple Sclerosis", Last Updated Mar. 8, 2023 (11 pages).
ClinicalTrials.gov ID No. NCT03996291, "Long Term Safety and Efficacy Study of Tolebrutinib (SAR442168) in Participants with Relapsing Multiple Sclerosis", Last Updated Apr. 24, 2023 (8 pages).
ClinicalTrials.gov ID No. NCT04171310, "Study of Excretion Balance and Pharmacokinetics of [14C]-SAR442168 in Healthy Male Subjects", Last Updated Apr. 25, 2022 (7 pages).
ClinicalTrials.gov ID No. NCT04410978, "Relapsing Forms of Multiple Sclerosis (RMS) Study of Bruton's Tyrosine Kinase (BTK) Inhibitor Tolebrutinib (SAR442168) (Gemini 1)", Last Updated Aug. 8, 2022 (11 pages).
ClinicalTrials.gov ID No. NCT04410991, "Relapsing Forms of Multiple Sclerosis (RMS) Study of Bruton's Tyrosine Kinase (BTK) Inhibitor Tolebrutinib (SAR442168) (Gemini 2)", Last Updated Aug. 8, 2022 (9 pages).
ClinicalTrials.gov ID No. NCT04411641, "Nonrelapsing Secondary Progressive Multiple Sclerosis (NRSPMS) Study of Bruton's Tyrosine Kinase (BTK) Inhibitor Tolebrutinib (SAR442168) (Hercules)", Last Updated Feb. 10, 2023 (9 pages).

(56) References Cited

OTHER PUBLICATIONS

ClinicalTrials.gov ID No. NCT04458051, "Primary Progressive Multiple Sclerosis (PPMS) Study of Bruton's Tyrosine Kinase (BTK) Inhibitor Tolebrutinib (SAR442168) (Perseus)", Last Updated Feb. 1, 2023 (9 pages).
ClinicalTrials.gov ID No. NCT05282030, "Study to Assess the Plasma Concentration of Tolebrutinib Given as a Tablet to Adult Participants With Renal Impairment Compared to Healthy Participants", Last Updated Jan. 26, 2023 (8 pages).
EU Clinical Trials Register No. 2018-003927-12, "A Phase2b dose-finding study for SAR442168, a Bruton's tyrosine kinase inhibitor, in participants with relapsing multiple sclerosis", first entered into EudraCT Jan. 11, 2019 (5 pages).
EU Clinical Trials Register No. 2018-004731-76, "Long-term extension safety and efficacy study of SAR442168 in participants with relapsing multiple sclerosis", first entered into EudraCT Feb. 25, 2019 (6 pages).
EU Clinical Trials Register No. 2020-000637-41, "A Phase 3, randomized, double-blind efficacy and safety study comparing SAR442168 to teriflunomide (Aubagio®) in participants with relapsing forms of multiple sclerosis", first entered into EudraCT Jun. 17, 2020 (7 pages).
EU Clinical Trials Register No. 2020-000644-55, "A Phase 3, randomized, double-blind efficacy and safety study comparing SAR442168 to teriflunomide (Aubagio®) in participants with relapsing forms of multiple sclerosis", first entered into EudraCT Jun. 15, 2020 (7 pages).
EU Clinical Trials Register No. 2020-000645-14, A Phase 3, randomized, double-blind, efficacy and safety study comparing SAR442168 to placebo in participants with primary progressive multiple sclerosis (PERSEUS), first entered into EudraCT Jul. 27, 2020 (6 pages).
EU Clinical Trials Register No. 2020-00647-30, "A Phase 3, randomized, double-blind, efficacy and safety study comparing SAR442168 to placebo in participants with nonrelapsing secondary progressive multiple sclerosis", first entered into EudraCT Jun. 16, 2020 (6 pages).
EU Clinical Trials Register No. 2021-003898-59, "A Phase 3, randomized, double-blind, placebo-controlled, parallel- group study to evaluate the efficacy and safety of tolbrutinib (SAR442168) in adults with generalized myasthenia gravis (MG)", first entered into EudraCT Oct. 6, 2021 (7 pages).
Smith P F et.al., "Phase 1 clinical trial of PRN2246 (SAR441268), a covalent BTK inhibitor demonstrates safety, CNS exposure and therapeutic levels of BTK occupancy", Database accession No. EMB 628003781 abstract & Multiple Sclerosis Journal 20190401 Sage Publications LTD NLD, vol. 25, No. Supplement 1, Apr. 1, 2019 (Apr. 1, 2019) (52 pages).
Sormani M P, et al., "Magnetic resonance imaging as a potential surrogate for relapses in multiple sclerosis: a meta-analytic approach.", Ann Neurol., 65(3), pp. 268-275 (2009).
Sormani M P, et al., "Surrogate endpoints for EDSS worsening in multiple sclerosis a meta-analytic approach.", Neurology, 75(4), pp. 302-309 (2010).
Study Record for ClinicalTrials.gov ID No. NCT04742400, "Tolebrutinib, a Brain-penetrant Bruton s Tyrosine Kinase Inhibitor, for the Modulation of Chronically Inflamed White Matter Lesions in Multiple Sclerosis", Last Updated Jul. 3, 2023 (12 pages).
Study Record for ClinicalTrials.gov ID No. NCT05283915, "Study to Assess the Plasma Concentration of Tolebrutinib Given as a Tablet to Adult Participants with Mild Hepatic Impairment Compared to Participants With Normal Hepatic Function", Last Updated Nov. 8, 2022 (8 pages).
Stys P K, et al. "Will the real multiple sclerosis please stand up?", Nat Rev Neurosci., 13(7), pp. 507-514 (2012).
Thompson A J, et al., "Diagnosis of multiple sclerosis: 2017 revisions of the McDonald criteria.", Lancet Neurol., 17(2), pp. 162-173 (2018).
Traboulsee Anthony et al., "Design of a Phase 2b Dose-finding Trial to Evaluate Safety and Efficacy of the CNS-penetrant BTK Inhibitor SAR442168 in Patients with Relapsing Forms of Multiple Sclerosis (804) : Neurology", Neurology, Apr. 14, 2020 (Apr. 14, 2020), XP055794139, Retrieved from the Internet: URL:https://n.neurology.org/content/94/15 Supplement/804. abstract—[retrieved by ISA on Apr. 12, 2021].
Coles et al., "Monoclonal antibody treatment exposes three mechanisms underlying the clinical course of multiple sclerosis", Ann Neurol, 46(3), pp. 296-304 (1999).
Confavreux et al., "Natural history of multiple sclerosis: a unifying concept", Brain., 129(Pt 3), pp. 606-616 (Mar. 2006).
Corneth et al., "BTK Signaling in B Cell Differentiation and Autoimmunity. In: Kurosaki T., Wienands J. (eds) B Cell Receptor Signaling", Current Topics in Microbiology and Immunology, vol. 393. Springer, Cham. https://doi.org/10.1007/82_2015_478 (2015).
Cottrell et al., "The natural history of multiple sclerosis: a geographically based study. 5. The clinical features and natural history of pimary progressive multiple sclerosis", Brain, 122, pp. 625-639 (1999).
Crawford et al., "Discovery of GDC-0853: A Potent, Selective, and Noncovalent Bruton's Tyrosine Kinase Inhibitor in Early Clinical Development", J Med Chem., 22;61(6), pp. 2227-2245 (2018).
Cron, et al. "Thymus involvement in early-onset myasthenia gravis", Ann N Y Acad Sci., 1412(1), pp. 137-145 (Jan. 2018).
Debouverie et al., "Multiple sclerosis with a progressive course from onset in Lorraine-Eastern France", J Neurol, 254, pp. 1370-1375 (2007).
Deenen et al., "The Epidemiology of Neuromuscular Disorders: A Comprehensive Overview of the Literature", J Neuromuscul Dis., 2(1), pp. 73-85 (2015).
Dendrou et al., "Immunopathology of multiple sclerosis", Nature Reviews Immunology, 15, pp. 545-558 (2015).
Di Paolo, et al., "Specific Btk inhibition suppresses B cell- and myeloid cell-mediated arthritis", Nature Chemical Biology, vol. 7, pp. 41-50 (Jan. 2011).
Duquette et al., "Multiple sclerosis in childhood: Clinical profile in 125 patients", Journal of Pediatrics, 111, pp. 359-363 (1987).
EMD Serono Inc., "Positive lake-breaking Phase II data evaluating investigational oral therapy, evobrutinib in RMS [Online]", Oct. 12, 2018 [cited Aug. 10, 2021]. Available from: URL:http://media.emdserono.com/press-releases?item=122714.
Erickson et al., "Bruton's Tyrosine Kinase Small Molecule Inhibitors Induce a Distinct Pancreatic Toxicity in Rats." J Pharmacol Exp Ther. 2017;360(1):226-38.
Ethnic Factors in The Acceptability of Foreign Clinical Data E5(R1) http://www.ich.org.
European Medicines Agency. "Guideline on the investigation of drug interactions." Jun. 21, 2012.
Evans et al., "Inhibition of Btk with CC-292 Provides Early Pharmacodynamic Assessment of Activity in Mice and Humans", J Pharmacol Exp Ther, 346(2), pp. 219-228 (Aug. 2013).
Evoli A., "Acquired myasthenia gravis in childhood", Curr Opin Neurol., 23(5), pp. 536-540 (Oct. 2010).
Fadda et al., "Canadian Pediatric Demyelinating Disease Network. MRI and laboratory features and the performance of international criteria in the diagnosis of multiple sclerosis in children and adolescents: a prospective cohort study", Lancet Child Adolesc Health., 2(3), pp. 191-204 (Mar. 2018).
FDA Center for Drug Evaluation and Research. In Vitro Drug Interaction Studies—Cytochrome P450 Enzyme- and Transporter-Mediated Drug Interactions Guidance for Industry. Jan. 2020.
FDA Guidance for Industry: Estimating the maximum safe starting dose in initial clinical trials for therapeutics in adult healthy volunteers. Jul. 2005.
Fu et al., "Ocular toxicities associated with targeted anticancer agents: an analysis of clinical data with management suggestions", Oncotarget, 8(35), pp. 58709-58727 (May 2017).
Futatani et al., "Bruton's tyrosine kinase is present in normal platelets and its absence identifies patients with X-linked agammaglobulinaemia and carrier females", Br J Haematol., 114(1), pp. 141-149 (2001).
Ghezzi et al., "Long-Term Effect of Immediate Versus Delayed Fingolimod Treatment in Young Adult Patients with Relapsing-

(56) References Cited

OTHER PUBLICATIONS

Remitting Multiple Sclerosis: Pooled Analysis from the Freedoms/Freedoms II Trials", Neurology and Therapy, 8, pp. 461-475 (2019).
Ghezzi et al., "Multiple sclerosis in childhood: clinical features of 149 cases", Multiple Sclerosis, 3, pp. 443-446 (1997).
Gilhus et al., "Myasthenia gravis", Nat Rev Dis Primers., 5(30), pp. 1-19 (2019).
Gilhus et al., "Myasthenia gravis: subgroup classification and therapeutic strategies", Lancet Neurol., 14(10), pp. 1023-1036 (Oct. 2015).
Giovannoni et al., "The COVID-19 pandemic and the use of MS disease-modifying therapies" [published online ahead of print, Mar. 27, 2020]. Mult Scler Relat Disord., vol. 39, 102073 (Apr. 2020).
Gough et al., "Assessment of dose proportionality: report from the statisticians in the pharmaceutical industry / pharmacokinetics UK joint working party", Drug Information J, 29, pp. 1039-1048 (1995).
Harding et al., "Modelling the Natural History of Primary Progressive Multiple Sclerosis", J Neurol Neurosurg Psychiatry, 86(1), pp. 13-19 (Jan. 2015).
Hata et al., "Involvement of Bruton's tyrosine kinase in FcepsilonRI-dependent mast cell degranulation and cytokine production", J Exp Med., 187(8), pp. 1235-1247 (1998).
Hauser et al., "B-Cell Depletion with Rituximab in Relapsing-Remitting Multiple Sclerosis", N Engl J Med., 358, pp. 676-688 (2008).
Hehir et al., "Generalized Myasthenia Gravis: Classification, Clinical Presentation, Natural History, and Epidemiology", Neurol Clin., 36(2), pp. 253-260 (May 2018).
Holcmann et al., "Mechanisms underlying skin disorders induced by EGFR inhibitors", Mol Cell Oncol., 2(4): e1004969 (Jun. 2015).
Honigberg et al., "The Bruton tyrosine kinase inhibitor PCI-32765 blocks B-cell activation and is efficacious in models of autoimmune disease and B-cell malignancy", Proc. Natl Acad Sci USA, 107(29), pp. 13075-13080 (Jul. 20, 2010).
Horwood et al., "Bruton's tyrosine kinase is required for lipopolysaccharide induced tumor necrosis factor alpha production", J Exp Med, 197(12), pp. 1603-1611 (2003).
Howard et al., "QMG and MG-ADL Correlations: Study of Eculizumab Treatment of Myasthenia Gravis", Muscle & Nerve, 56(2), pp. 328-330 (Aug. 2017).
Howard et al., "Safety and efficacy of eculizumab in anti-acetylcholine receptor antibody-positive refractory generalized myasthenia gravis (REGAIN): a phase 3, randomised, double-blind, placebo-controlled, multicentre study", Lancet Neurol., 16(12), pp. 976-986 (Dec. 2017).
http://evs.nci.nih.gov/ftp1/CTCAE/CTCAE_4.03_2010-06-14_QuickReference_5x7.pdf.
Huang et al., "Clinical characteristics of juvenile myasthenia gravis in southern China Front", Neurol., 9, p. 77 (2018).
Hundelshausen et al., "Bleeding by Bruton tyrosine kinase-inhibitors: Dependency on drug type and disease", Cancers, 13(5), p. 1103 (Jan. 2021).
Hutcheson et al., "Modulating proximal cell signaling by targeting Btk ameliorates humoral autoimmunity and end-organ disease in murine lupus", Arthritis Res Ther., 14: R243 (2012).
Ibrahim et al., "The power prior: theory and applications", Statist. Med., 34, pp. 3724-3749 (2015).
Ibrutinib [prescribing information]. Horsham, PA: Janssen Biotech, Inc.; 2013 [Revised Jan. 2015; cited Aug. 12, 2021]. Available from: https://www.accessdata.fda.gov/drugsatfda_docs/label/2015/205552s002lbl.pdf.
Imbruvica [package insert]. Pharmacyclics, Inc., Sunnyvale, CA; 2017.
Ingle et al., "Magnetic resonance imagin in primary progressive multiple sclerosis", Journal of Rehabilitation Research and Development, 39(2), pp. 261-272 (Mar./Apr. 2002).
Irwin, S., "Comprehensive observational assessment: la. A systematic, quantitative procedure for assessing the behavioral and physiologic state of the mouse", Psychopharmacologia, 13(3), pp. 222-257 (1968).
Itachaki et al., "Experience with ibrutinib for first-line use in patients with chronic lymphocytic leukemia", Ther Adv Hematol., 9(1), pp. 3-19 (Jan. 2018).
Jaretzki et al., "Myasthenia gravis: recommendations for clinical research standards. Task Force of the Medical Scientific Advisory Board of the Myasthenia Gravis Foundation of America", Neurology, 55(1), pp. 16-23 (Jul. 12, 2000).
Johnson, "Modelling approaches to dose estimation in children", Br J Clin Pharmacol, 59(6), pp. 663-669 (2005).
Jolas, "In Vitro Pharmacology: Study of RA15590545", Eurofins Cerep No. 100045701_NP-062-18C (Sep. 3, 2018).
Shi et al., "Purine derivatives as potent Bruton's tyrosine kinase (BTK) inhibitors for autoimmune diseases", Bioorganic & Medicinal Chemistry Letters, 24, pp. 2206-2211 (2014).

* cited by examiner

CRYSTALLINE FORM OF TOLEBRUTINIB

CROSS-REFERENCE TO RELATED APPLICATIONS

This application is a continuation of International Application No. PCT/CN2021/132028, filed Nov. 22, 2021, which claims the benefit of priority to Chinese Patent Application 202011455573.5, filed Dec. 10, 2020. The contents of each of the referenced applications are incorporated herein by reference in their entireties.

TECHNICAL FIELD

The present disclosure pertains to the field of chemical crystallography, particularly relates to crystalline forms of Tolebrutinib, preparation method and use thereof.

BACKGROUND

Multiple Sclerosis (MS) is a neurological disease affecting more than 1 million people worldwide. It is the most common cause of neurological disability in young and middle-aged adults and has a major physical, psychological, social and financial impact on subjects and their families. MS involves an immune-mediated process in which an abnormal response of the body's immune system is directed against the central nervous system (CNS). In the course of the disease, scleroses, i.e., lesions or scars, appear in the myelin sheath of nerve cells, disrupting transmission of electrical signals. Scleroses accumulate over time and result in the debilitating symptoms experienced by MS patients.

Immunomodulatory drugs have been the mainstay of MS therapy. Results from recent clinical studies have demonstrated efficacy of agents that target B lymphocytes.

The Bruton's tyrosine kinase (BTK) pathway is critical to signaling in B lymphocytes and myeloid cells including CNS microglia. Each of these cell types has been implicated in the pathophysiology of MS. Further, as BTK signaling is vital for maturation of B cells into antibody-secreting plasma cells, BTK inhibition can modulate both cellular and humoral immunity. Accordingly, an inhibitor of BTK signaling represents a dual mechanism targeting both aspects of the immune system.

Accordingly, compounds that inhibit BTK that are able to both inhibit antigen-induced B-cell activation responsible for neuroinflammation and modulate maladaptive microglia cells linked to neuroinflammation in the brain and spinal cord may be useful in treating relapsing multiple sclerosis (RMS) with superior benefits when compared to currently available therapies.

Tolebrutinib, an oral selective small-molecule BTK inhibitor, has shown safety and efficacy in patients with RMS.

The chemical name of Tolebrutinib is (R)-1-(1-acryloylpiperidin-3-yl)-4-amino-3-(4-phenoxyphenyl)-1H-imidazo[4,5-c]pyridin-2(3H)-one (hereinafter referred to as Compound I), and the structure is shown as follows:

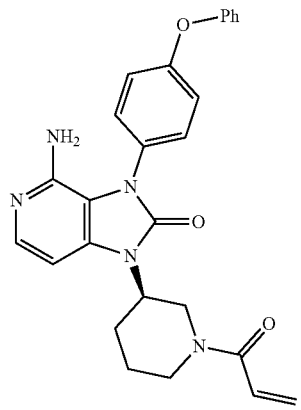

Compound I

A crystalline form is a solid material whose constituents are arranged in a highly ordered microscopic structure, forming a crystal lattice that extends in all directions. Polymorphism refers to the phenomenon that a compound exists in more than one crystalline form. Compounds may exist in one or more crystalline forms, but their existence and the characteristics cannot be predicted with any certainty. Different crystalline forms of drug substances have different physicochemical properties, which can affect drug's in vivo dissolution and absorption and will further affect drug's clinical efficacy to some extent. In particular, for some poorly soluble oral solid or semi-solid dosage forms, crystalline forms can be crucial to the performance of drug product. In addition, the physiochemical properties of a crystalline form are very important to the production process. Therefore, polymorphism is an important part of drug research and drug quality control.

A white solid of Compound I was disclosed in WO2016196840A1. The inventors of the present disclosure repeated the preparation process and an amorphous of Compound I was obtained. Furthermore, the inventors of the present disclosure have systematically evaluated the properties of the amorphous obtained, and the results show that the amorphous of Compound I has disadvantages such as poor stability, strong hygroscopicity and easy degradability, and is not suitable for medicine use.

In order to overcome the disadvantages of the prior arts, the inventors of present disclosure conducted a systematic study on Compound I and found that Compound I easily forms amorphous and is difficult to crystallize. Specifically, the inventors of present disclosure designed a large number of experiments including different processing methods, solvent systems and post-treatment processes, trying to obtain a solid form of Compound I with good physicochemical stability, good hygroscopicity and little degradability. While no crystalline form suitable for medicine use was obtained except for amorphous of Compound I. The inventors of present disclosure further tried more methods and surprisingly obtained a crystalline form of Compound I. This crystalline form has advantages in at least one aspect of solubility, hygroscopicity, purification ability, stability, adhesiveness, compressibility, flowability, in vitro and in vivo dissolution, bioavailability, etc. In particular, the crystalline form of Compound I of the present disclosure has advantages such as good stability, good hygroscopicity, and little degradability, which solves the problems existing in the prior art and is of great significance for the development of drugs containing Compound I.

SUMMARY

The present disclosure is to provide a novel crystalline form of Compound I, preparation method and use thereof.

According to the objective of the present disclosure, the crystalline form of Compound I is provided.

Furthermore, crystalline form CSI of Compound I is provided (hereinafter referred to as Form CSI).

In one aspect provided herein, the X-ray powder diffraction pattern of Form CSI comprises one or two or three characteristic peaks at 2theta values of 7.7°±0.2°, 11.0°±0.2° and 22.8°±0.2° using CuKα radiation. Preferably, the X-ray powder diffraction pattern of Form CSI comprises characteristic peaks at 2theta values of 7.7°±0.2°, 11.0°±0.2° and 22.8°±0.2° using CuKα radiation.

In another aspect provided herein, the X-ray powder diffraction pattern of Form CSI comprises one or two or three characteristic peaks at 2theta values of 12.0°±0.2°, 16.1°±0.2° and 18.5°±0.2° using CuKα radiation. Preferably, the X-ray powder diffraction pattern of Form CSI comprises characteristic peaks at 2theta values of 12.0°±0.2°, 16.1°±0.2° and 18.5°±0.2° using CuKα radiation.

In another aspect provided herein, the X-ray powder diffraction pattern of Form CSI comprises one or two or three characteristic peaks at 2theta values of 13.6°±0.2°, 20.1°±0.2° and 24.8°±0.2° using CuKα radiation. Preferably, the X-ray powder diffraction pattern of Form CSI comprises characteristic peaks at 2theta values of 13.6°±0.2°, 20.1°±0.2° and 24.8°±0.2° using CuKα radiation.

In another aspect provided herein, the X-ray powder diffraction pattern of Form CSI comprises one or two or three or four or five or six or seven or eight or nine characteristic peaks at 2theta values of 7.7°±0.2°, 11.0°±0.2°, 22.8°±0.2°, 12.0°±0.2°, 16.1°±0.2°, 18.5°±0.2°, 13.6°±0.2°, 20.1°±0.2°, 24.8°±0.2° and 18.7°±0.2° using CuKα radiation.

Without any limitation being implied, the X-ray powder diffraction pattern of Form CSI is substantially as depicted in FIG. 2 using CuKα radiation.

Without any limitation being implied, the DSC curve of Form CSI is substantially as depicted in FIG. 6, which shows an endothermic peak at around 170° C. (onset temperature). This peak is the melting endothermic peak.

Without any limitation being implied, the TGA curve of Form CSI is substantially as depicted in FIG. 5, which shows about 0.4% weight loss when heated from 31° C. to 160° C.

Without any limitation being implied, Form CSI is an anhydrate.

According to the objective of the present disclosure, a process for preparing Form CSI is also provided. The process comprises:

Adding the solid of Compound I into an ketone or an ether, stirring at a certain temperature and separating to obtain Form CSI.

Furthermore, said ketone is preferably a ketone of C3-C6, said ether is preferably an ether of C5.

Furthermore, said ketone is preferably 4-methyl-2-pentanone, said ether is preferably methyl tertiary butyl ether.

Furthermore, said stirring temperature is preferably from room temperature to 55° C., said stirring time is preferably more than 25 hours.

According to the objective of the present disclosure, the present disclosure provides the use of Form CSI for preparing other crystalline forms, or salts of Compound I.

According to the objective of the present disclosure, a pharmaceutical composition is provided, said pharmaceutical composition comprises a therapeutically effective amount of the crystalline form of Compound I and pharmaceutically acceptable excipients.

Furthermore, use of the crystalline form of Compound I is provided by present disclosure for the preparation of a BTK inhibitor drug.

Furthermore, use of the crystalline form of Compound I is provided by present disclosure for the preparation of a drug for the treatment of multiple sclerosis.

Furthermore, the crystalline form of Compound I is preferably Form CSI.

Technical Problems Solved by Present Disclosure

The inventors of the present disclosure studied the prior art and found that the prior art is the amorphous of Compound I. It is found through research that the amorphous of Compound I has disadvantages such as poor chemical stability, poor hygroscopicity and easy degradability, which is not suitable for medicine use and industrial production. In order to overcome the disadvantages of prior arts, a crystalline form of Compound I is provided by the present disclosure, which has excellent physical and chemical stability, good hygroscopicity, and is suitable for the development of drugs containing Compound I.

As shown in Example 1, Compound I is difficult to crystallize. Only amorphous was obtained by various crystallization methods. Even trying different crystallization methods and control the processing conditions in the preparation process, such as: solvent (alcohols, ketones, esters, ethers, acids, water, nitriles, amides, halogenated hydrocarbons, aromatic hydrocarbons, alkanes, sulfoxides, etc.), temperature, time, evaporation rate, additives and other factors, can only obtain amorphous. To obtain Form CSI of the present disclosure, the inventors further tried a variety of unconventional solvents and improved the preparation and post-treatment conditions based on the foregoing preparation methods. This shows that Form CSI provided by present disclosure is unpredictable for the skilled in the art.

Technical Effects

Form CSI of the present disclosure has the following unexpected advantages:

(1) The chemical purity of the prior art solid decreases significantly when stored under the conditions of 25° C./60% RH, 40° C./75% RH, 60° C./75% RH, and 80° C. In particular, after storage at 40° C./75% RH for 6 months with open package, the purity decreases by 3.46%, and the number of impurities which exceed the qualificated threshold increases to four. After storage at 60° C./75% RH for only 1 month with sealed package, the purity decreases by 2.76%, and the number of impurities which exceed the qualificated threshold increases to two. After storage at 60° C./75% RH for only 1 month with open package, the purity decreases over 6.3%, and the number of impurities which exceed the qualificated threshold increases to four. The chemical stability of the prior art solid is far below the medicinal standard.

Compared with the prior art, Form CSI drug substance of the present disclosure has good stability itself and in drug product. Crystalline state of Form CSI drug substance doesn't change for at least 6 months when stored under the condition of 25° C./60% RH with open and sealed package. The chemical purity is above 99.8% and remains substantially unchanged during storage. After Form CSI is mixed with the excipients to form a drug product and stored under the condition of 25° C./60% RH, crystalline state of Form CSI drug product doesn't change for at least 3 months. These results show that From CSI drug substance of the present disclosure has good stability under long term condition both itself and in drug product which is suitable for drug storage.

Meanwhile, the crystalline state of Form CSI drug substance doesn't change for at least 6 months when stored under the condition of 40° C./75% RH with open and sealed package. The crystalline state of Form CSI drug substance doesn't change for at least 1 month when stored under the condition of 60° C./75% RH with open or sealed package. The chemical purity is above 99.8% and remains substantially unchanged during storing. The chemical purity of Form CSI drug substance remains substantially unchanged for at least 2 days when stored under the condition of 80° C. After Form CSI is mixed with the excipients to form a drug product and stored under the condition of 40° C./75% RH, crystalline state of Form CSI drug product doesn't change for at least 3 months. These results show that Form CSI drug substance has better stability under accelerated and stress conditions both itself and in drug product. Generally, a drug substance and a drug product will go through high temperature and high humidity conditions caused by different seasons, regional climates and environments during storage, transportation, and manufacturing processes. Therefore, good stability under accelerated and stress conditions is of great importance to the drug development. Form CSI drug substance has good stability under stress conditions both itself and in drug product, which is beneficial to avoid the impact on drug quality due to crystal transformation or decrease in purity during drug storage.

In addition, the impurity content of Form CSI drug substance did not exceed the qualificated threshold throughout the stability investigation processes, which can meet the requirements of pharmaceutical development.

(2) Compared with prior art, Form CSI of the present disclosure has good hygroscopicity. The test results show that the weight gain of Form CSI is only ⅐ that of the prior art. The weight gain of Form CSI at 80% RH is 0.53%, indicating that Form CSI is slightly hygroscopic. The weight gain of the prior art solid at 80% RH is 3.69%, indicating that the prior art is hygroscopic. In one aspect, poor hygroscopicity tends to cause chemical degradation and polymorph transformation, which directly affects the physical and chemical stability of the drug substance. In addition, poor hygroscopicity will reduce the flowability of the drug substance, thereby affecting the processing of the drug substance.

In another aspect, drug substance with poor hygroscopicity requires low humidity environment during production and storage, which puts strict requirements on production and imposes higher costs. More importantly, poor hygroscopicity is likely to cause variation in the content of active pharmaceutical ingredients in the drug product, thus affecting drug product quality.

Form CSI provided by the present disclosure with good hygroscopicity is not demanding on the production and storage conditions, which reduces the cost of production, storage and quality control, and has strong economic value.

DETAILED DESCRIPTION

Figure 1:
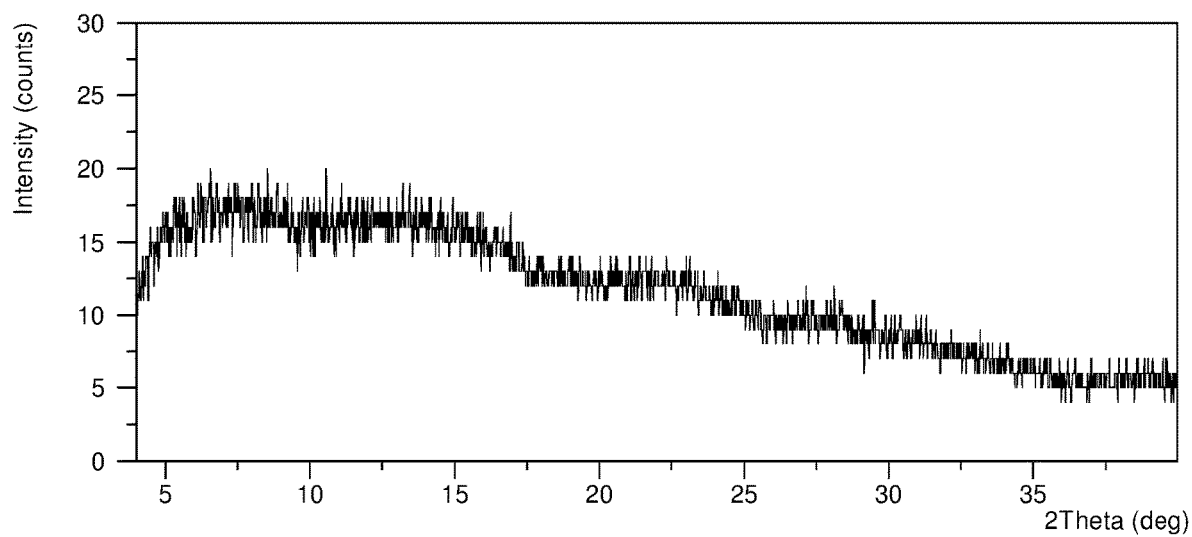
FIG. 1 shows an XRPD pattern of sample 1 according to example 1.

The present disclosure is further illustrated by the following examples which describe the preparation and use of the crystalline forms of the present disclosure in detail. It is obvious to those skilled in the art that changes in the materials and methods can be accomplished without departing from the scope of the present disclosure.

The abbreviations used in the present disclosure are explained as follows:
XRPD: X-ray Powder Diffraction
DSC: Differential Scanning Calorimetry
TGA: Thermo Gravimetric Analysis
DVS: Dynamic Vapor Sorption
$^1$H NMR: Proton Nuclear Magnetic Resonance
RH: Relative humidity
UPLC: Ultra Performance Liquid Chromatography
LC: Liquid Chromatography
PE: Polyethylene
LDPE: Low Density Polyethylene
HDPE: High Density Polyethylene Instruments and Methods Used for Data Collection:
X-ray powder diffraction patterns in the present disclosure were acquired by a Bruker X-ray powder diffractometer. The parameters of the X-ray powder diffraction method of the present disclosure are as follows:
X-Ray: Cu, Kα
Kα1 (Å): 1.54060; Kα2 (Å): 1.54439
Kα2/Kα1 intensity ratio: 0.50
Thermo gravimetric analysis (TGA) data in the present disclosure were acquired by a TA Q500.
The parameters of the TGA method of the present disclosure are as follows:
Heating rate: 10° C./min
Purge gas: nitrogen
Differential scanning calorimetry (DSC) data in the present disclosure were acquired by a TA Q2000. The parameters of the DSC method of the present disclosure are as follows:
Heating rate: 10° C./min
Purge gas: nitrogen Dynamic Vapor Sorption (DVS) was measured via an SMS (Surface Measurement Systems Ltd.) intrinsic DVS instrument. Typical Parameters for DVS test are as follows:

Temperature: 25° C.

Gas and flow rate: nitrogen, 200 mL/min

RH range: 0% RH to 95% RH

Proton nuclear magnetic resonance spectrum data ($^1$H NMR) were collected from a Bruker Avance II DMX 400M HZ NMR spectrometer. 1-5 mg of sample was weighed and dissolved in 0.5 mL of deuterated dimethyl sulfoxide to obtain a solution with a concentration of 2-10 mg/mL.

The related substance in the present disclosure was detected by UPLC and the parameters are shown below.

TABLE 1

| Instrument | Waters ACQUITY UPLC H-Class with PDA |  |
|---|---|---|
| Column | ACE Excel 3 C18 |  |
| Mobile phase | A: 0.1% $H_3PO_4$ in $H_2O$ (pH4.0, TEA) |  |
|  | B: Acetonitrile |  |
| Gradient | Time (min) | % B |
|  | 0.0 | 10 |
|  | 0.3 | 10 |
|  | 3.5 | 45 |
|  | 9.0 | 80 |
|  | 11.0 | 80 |
|  | 11.1 | 10 |
|  | 18.0 | 10 |
| Run time | 18.0 min |  |
| Stop time | 0.0 min |  |
| Injection volume | 1 μL |  |
| Detector wavelength | 226 nm |  |
| Column temperature | 40° C. |  |
| Sample temperature | Room temperature |  |
| Diluent | 0.01% TFA in Acetonitrile |  |

In the present disclosure, said "stirring" is accomplished by using a conventional method in the field such as magnetic stirring or mechanical stirring and the stirring speed is 50 to 1800 r/min. Preferably the magnetic stirring speed is 300 to 900 r/min and mechanical stirring speed is 100 to 300 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished by using a conventional method in the field such as vacuum drying, blast drying or free-air drying. The drying temperature can be room temperature or higher. Preferably the drying temperature is from room temperature to about 60° C., or to 50° C., or to 40° C. The drying time can be 2 to 48 hours, or overnight. Drying is accomplished in a fume hood, forced air convection oven or vacuum oven.

Said "room temperature" is not a specific temperature, but a temperature range of 10-30° C.

Said "open packaged" is putting the sample into a glass vial, covering the vial with aluminum foil, and punching 5-10 holes on the foil.

Said "sealed packaged" is putting the sample into a glass vial, capping the vial tightly, and sealing the vial in an aluminum foil bag.

Said "characteristic peak" refers to a representative diffraction peak used to distinguish crystals, which usually can have a deviation of 0.2° using CuKα radiation.

In the present disclosure, "crystal" or "crystalline form" refers to the crystal or the crystalline form being identified by the X-ray diffraction pattern shown herein. Those skilled in the art are able to understand that the experimental errors depend on the instrument conditions, the sample preparation and the purity of samples. The relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. Thus, it will be understood by those skilled in the art that a crystalline form of the present disclosure is not necessarily to have exactly the same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CSI of the present disclosure is pure and substantially free of any other crystalline forms. In the present disclosure, the term "substantially free" when used to describe a novel crystalline form, means that the content of other crystalline forms in the novel crystalline form is less than 20% (w/w), specifically less than 10% (w/w), more specifically less than 5% (w/w) and furthermore specifically less than 1% (w/w).

In the present disclosure, the term "about" when referring to a measurable value such as weight, time, temperature, and the like, is meant to encompass variations of ±10%, ±5%, ±1%, ±0.5%, or even ±0.1% of the specified amount.

Unless otherwise specified, the following examples were conducted at room temperature.

According to the present disclosure, Compound I and/or its salt used as a raw material is solid (crystalline or amorphous), oil, liquid form or solution. Preferably, Compound I used as a raw material is a solid.

Raw materials of Compound I and/or a salt thereof used in the following examples were prepared by known methods in the prior art, for example, the method disclosed in WO2016196840A1.

Example 1: Attempts for Preparing Compound I Solid Form

The inventors of the present disclosure tried various methods and regulated various process conditions for preparing solid forms, such as solvent (alcohols, ketones, esters, ethers, acids, water, nitriles, amides, halogenated hydrocarbons, aromatic hydrocarbons, alkanes, sulfoxides, etc.), temperature, time, evaporation rate, additives, and other factors. More than one hundred experiments were carried out, while only amorphous was obtained. Some of the experimental methods and results are listed in Table 2-6.

TABLE 2

| Methods | Regulated influencing factors | Results |
|---|---|---|
| Stirring | Solvent (alcohols, esters, acids, water, nitriles, aromatic hydrocarbons, mixtures thereof, etc.), temperature, time | Amorphous |
| Evaporation | Solvent (alcohols, ketones, esters, ethers, acids, water, halogenated hydrocarbons, amides, mixtures thereof, etc.), additives, time, evaporation rate | Amorphous |
| Solid vapor diffusion | Solvent (alcohols, esters, ethers, water, alkanes, amides, sulfoxides, etc.), temperature | Amorphous |
| Liquid vapor diffusion | Solvent (alcohols, ketones, esters, ethers, acids, water, alkanes, amides, sulfoxides, etc.), time | Amorphous |
| Summary | Solvent (alcohols, ketones, esters, ethers, acids, water, nitriles, amides, halogenated hydrocarbons, aromatic hydrocarbons, alkanes, sulfoxides, etc.), temperature, time, evaporation rate, additives | Amorphous |

Method 1: Stirring

According to Table 3, a certain mass of Compound I solid was weighed into a glass vial, followed by an addition of a certain volume of solvent. After stirring at certain temperature for a period, the solid was separated. All the obtained solids were confirmed to be amorphous by XRPD. The XRPD pattern of sample 1 is substantially as depicted in FIG. 1.

TABLE 3

| Sample | Weight (mg) | Solvent (v/v) | Volume (mL) | Temperature (° C.) | Stirring time | Solid form |
|---|---|---|---|---|---|---|
| 1 | 9.6 | Methanol | 0.2 | Room temperature | 1 day | Amorphous |
| 2 | 8.9 | Ethyl acetate | 0.2 | Room temperature | 1 day | Amorphous |
| 3 | 9.9 | Toluene | 0.2 | Room temperature | 1 day | Amorphous |
| 4 | 9.8 | Water | 0.2 | Room temperature | 1 day | Amorphous |
| 5 | 9.2 | Acetonitrile | 0.2 | Room temperature | 1 day | Amorphous |
| 6 | 19.0 | Isopropyl alcohol | 0.2 | 50 | 1 day | Amorphous |
| 7 | 17.9 | Acetic acid/Water (36/64) | 0.2 | 50 | 1 day | Amorphous |
| 8 | 18.1 | Isopropyl acetate | 0.4 | 50 | 5 days | Amorphous |

Method 2: Evaporation

According to Table 4, a certain mass of Compound I solid was weighed into a glass vial. After adding a certain volume of solvent and an additive, the system was evaporated at room temperature. All the obtained solids were confirmed to be amorphous by XRPD.

TABLE 4

| Sample | Weight (mg) | Solvent (v/v) | Volume (mL) | Additive | Time | Evaporation rate | Solid form |
|---|---|---|---|---|---|---|---|
| 1 | 8.7 | Chloroform | 0.2 | N/A | 4 days | Slow | Amorphous |
| 2 | 8.0 | Tetrahydrofuran | 0.2 | N/A | 4 days | Slow | Amorphous |
| 3 | 8.0 | Ethyl acetate | 0.6 | N/A | 4 days | Slow | Amorphous |
| 4 | 8.5 | Acetone/Water (97/3) | 1.0 | N/A | 4 days | Slow | Amorphous |
| 5 | 7.6 | Acetone/Water (91/9) | 1.0 | N/A | 4 days | Slow | Amorphous |
| 6 | 8.0 | N,N-Dimethylformamide/Water (94/6) | 1.0 | N/A | 4 days | Slow | Amorphous |
| 7 | 7.6 | Propionic acid | 0.4 | Polyacetal | 1 month | Fast | Amorphous |
| 8 | 8.4 | Tetrahydrofuran/Methanol (3/2) | 1.6 | Chlorosulfonated polyethylene | 4 days | Fast | Amorphous |

Method 3: Solid Vapor Diffusion

According to Table 5, a certain mass of Compound I solid was weighed into a glass vial. The vial was put into a larger glass vial containing about 5 mL of corresponding solvent. The larger vial was sealed with a cap and placed at a certain temperature for sufficient contact of solvent atmosphere and the solid in the vial. All the solids were taken out for XRPD test after 1 day and were confirmed to be amorphous.

TABLE 5

| Sample | Weight (mg) | Solvent | Temperature (° C.) | Solid form |
|---|---|---|---|---|
| 1 | 7.0 | n-Hexane | Room temperature | Amorphous |
| 2 | 8.0 | Water | Room temperature | Amorphous |
| 3 | 7.6 | Dimethyl sulfoxide | Room temperature | Amorphous |
| 4 | 9.9 | N,N-Dimethylacetamide | Room temperature | Amorphous |
| 5 | 13.0 | Benzyl alcohol | 5 | Amorphous |
| 6 | 9.7 | L-Ethyl lactate | 5 | Amorphous |
| 7 | 13.1 | Petroleum ether | 5 | Amorphous |
| 8 | 11.3 | 1,3-Dioxolane | 5 | Amorphous |

Method 4: Liquid Vapor Diffusion

According to Table 6, a certain mass of Compound I solid was weighed into a glass vial and dissolved with a certain volume of solvent. The vial was put into a larger glass vial containing about 5 mL of corresponding anti-solvents, then the larger vial was sealed with a cap and placed at a certain temperature to allow the anti-solvent vapor diffusing into the inner vial sufficiently. All the solids were isolated and confirmed to be amorphous by XRPD after diffusion for different times.

TABLE 6

| Sample | Weight (mg) | Solvent | Volume (mL) | Anti-solvent | Time | Solid form |
|---|---|---|---|---|---|---|
| 1 | 9.8 | Acetic acid | 0.2 | Methanol | 86 days | Amorphous |
| 2 | 10.3 | Acetic acid | 0.3 | Methyl tert-butyl ether | 86 days | Amorphous |
| 3 | 11.0 | Dimethyl sulfoxide | 0.3 | Isopropyl acetate | 86 days | Amorphous |
| 4 | 11.7 | Dimethyl sulfoxide | 0.3 | n-Hexane | 86 days | Amorphous |
| 5 | 9.7 | N-methylpyrrolidone | 0.3 | Methyl isobutyl ketone | 86 days | Amorphous |
| 6 | 10.3 | N,N-dimethylacetamide | 0.3 | Water | 1 day | Amorphous |
| 7 | 11.8 | N,N-dimethylformamide | 0.3 | Water | 9 days | Amorphous |
| 8 | 12.4 | N,N-dimethylformamide | 0.3 | Methyl tert-butyl ether | 86 days | Amorphous |

The above experimental results indicate that Compound I is difficult to crystallize and amorphous is easily obtained. The inventors of the present disclosure further tried various unconventional solvents and improved the preparation and post-treatment conditions, as described in Example 2-4, and the crystal form of Compound I was finally obtained unexpectedly.

Figure 2:
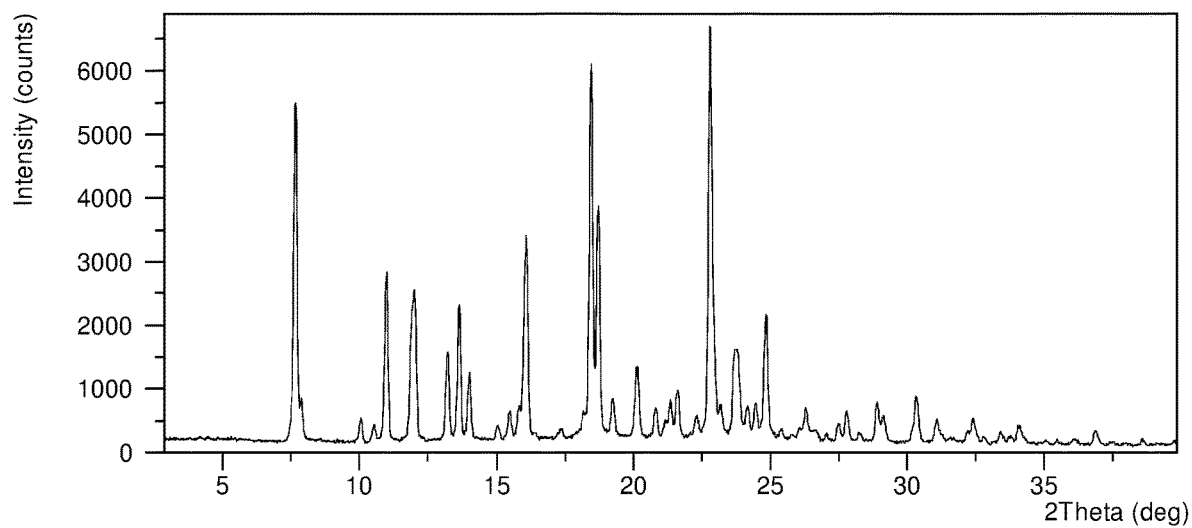
FIG. 2 shows an XRPD pattern of Form CSI according to example 2.

Example 2: Preparation Method of Form CSI 300.8 mg of Compound I solid was weighed into a 3-mL glass vial, followed by the addition of 2.0 mL of methyl isobutyl ketone. After stirring at 50° C. for about 39 hours, a solid was isolated. The obtained solid is confirmed to be Form CSI of the present disclosure. The XRPD pattern is substantially as depicted in FIG. 2, and the XRPD data are listed in Table 7.

TABLE 7

| 2θ (°) | d spacing (Å) | Relative intensity (%) |
|---|---|---|
| 7.69 | 11.50 | 81.95 |
| 7.89 | 11.21 | 10.33 |
| 10.07 | 8.78 | 5.49 |
| 10.55 | 8.39 | 4.24 |
| 11.00 | 8.04 | 41.35 |
| 11.88 | 7.45 | 26.12 |
| 12.04 | 7.35 | 34.15 |
| 13.22 | 6.70 | 21.79 |
| 13.64 | 6.49 | 33.48 |
| 14.02 | 6.32 | 16.90 |
| 15.02 | 5.90 | 3.83 |
| 15.47 | 5.73 | 7.44 |
| 15.80 | 5.61 | 8.05 |
| 16.10 | 5.51 | 47.60 |
| 17.36 | 5.11 | 3.12 |
| 18.47 | 4.80 | 92.44 |
| 18.73 | 4.74 | 57.54 |
| 19.24 | 4.61 | 10.58 |
| 20.14 | 4.41 | 18.59 |
| 20.83 | 4.26 | 8.44 |
| 21.36 | 4.16 | 10.50 |
| 21.62 | 4.11 | 12.80 |
| 22.30 | 3.99 | 6.58 |
| 22.79 | 3.90 | 100.00 |
| 23.66 | 3.76 | 21.01 |
| 23.83 | 3.73 | 21.02 |
| 24.18 | 3.68 | 8.80 |
| 24.46 | 3.64 | 9.62 |
| 24.85 | 3.58 | 31.33 |

TABLE 7-continued

| 2θ (°) | d spacing (Å) | Relative intensity (%) |
|---|---|---|
| 26.29 | 3.39 | 8.42 |
| 27.45 | 3.25 | 4.21 |
| 27.77 | 3.21 | 7.89 |
| 28.25 | 3.16 | 2.45 |
| 28.89 | 3.09 | 9.70 |
| 29.14 | 3.06 | 6.68 |
| 30.32 | 2.95 | 11.30 |
| 31.09 | 2.88 | 6.06 |
| 32.41 | 2.76 | 5.91 |
| 33.41 | 2.68 | 2.46 |

TABLE 7-continued

| 2θ (°) | d spacing (Å) | Relative intensity (%) |
|---|---|---|
| 34.08 | 2.63 | 4.17 |
| 36.11 | 2.49 | 1.14 |
| 36.84 | 2.44 | 3.09 |

Figure 3:
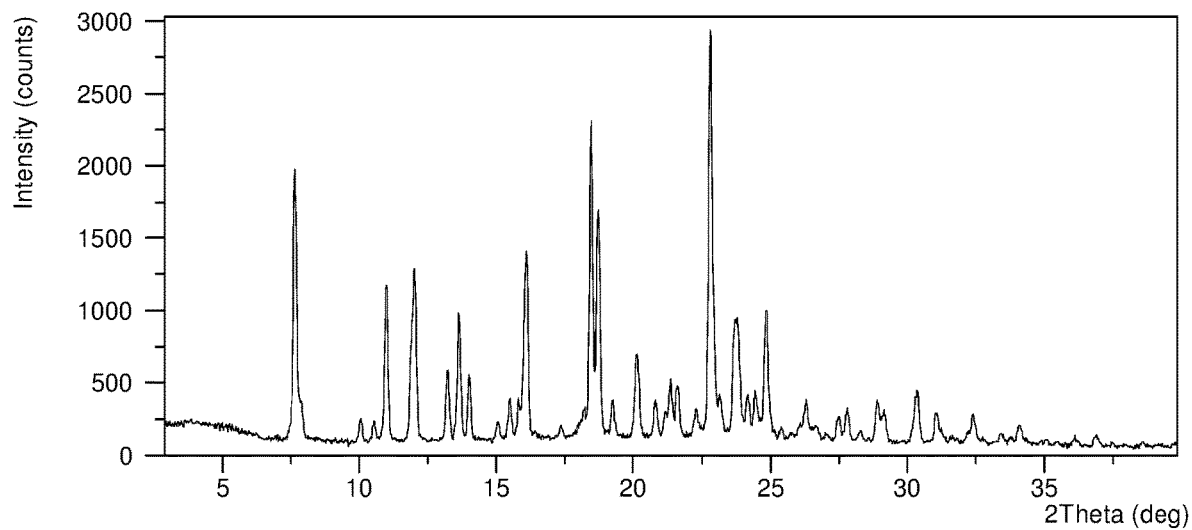
FIG. 3 shows an XRPD pattern of Form CSI according to example 3.
Figure 4:
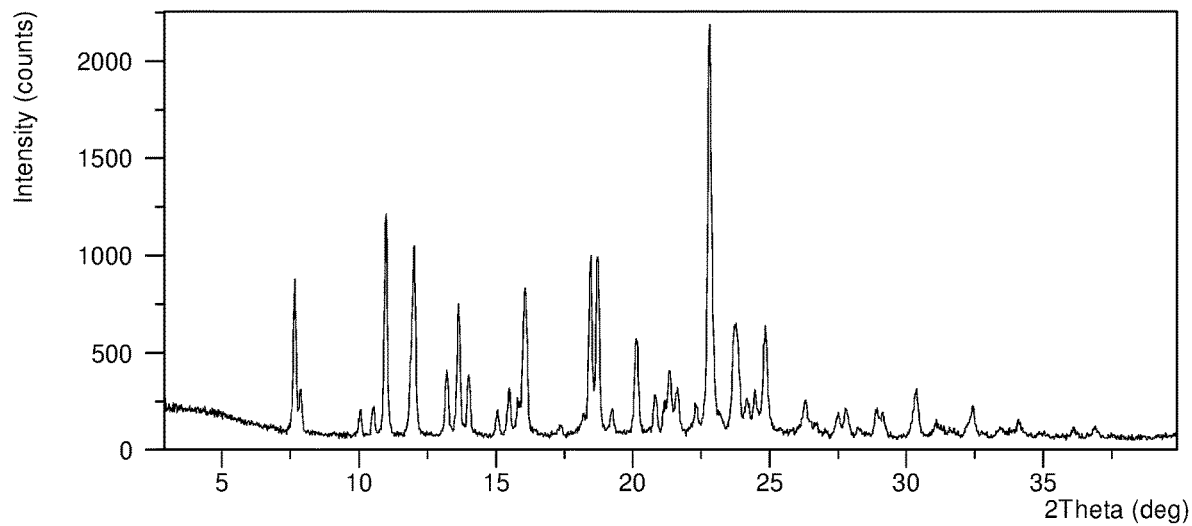
FIG. 4 shows an XRPD pattern of Form CSI according to example 4.

Example 3: Preparation Method of Form CSI 300.1 mg of Compound I solid was weighed into a 3-mL glass vial, followed by the addition of 2.0 mL of methyl isobutyl ketone. After stirring at 50° C. for about 6 days, a solid was isolated. The obtained solid is confirmed to be Form CSI of the present disclosure by XRPD. The XRPD pattern is substantially as depicted in FIG. 3, and the XRPD data are listed in Table 8.

TABLE 8

| 2θ (°) | d spacing (Å) | Relative intensity (%) |
|---|---|---|
| 7.64 | 11.57 | 64.68 |
| 10.06 | 8.79 | 5.16 |
| 10.53 | 8.40 | 4.30 |
| 10.98 | 8.06 | 37.82 |
| 12.03 | 7.36 | 40.10 |
| 13.21 | 6.70 | 17.22 |
| 13.63 | 6.50 | 31.16 |
| 14.00 | 6.32 | 16.13 |
| 15.04 | 5.89 | 4.71 |
| 15.47 | 5.73 | 10.37 |
| 15.79 | 5.61 | 10.80 |
| 16.09 | 5.51 | 46.03 |
| 17.36 | 5.11 | 3.85 |
| 18.46 | 4.81 | 76.52 |
| 18.73 | 4.74 | 56.08 |
| 19.26 | 4.61 | 10.27 |
| 20.12 | 4.41 | 21.12 |
| 20.81 | 4.27 | 10.44 |
| 21.36 | 4.16 | 15.59 |
| 21.63 | 4.11 | 13.59 |
| 22.29 | 3.99 | 7.89 |
| 22.79 | 3.90 | 100.00 |
| 23.68 | 3.76 | 27.31 |
| 23.82 | 3.74 | 29.20 |
| 24.15 | 3.69 | 11.27 |
| 24.44 | 3.64 | 12.52 |
| 24.83 | 3.59 | 32.01 |
| 26.31 | 3.39 | 10.77 |
| 27.43 | 3.25 | 5.57 |
| 27.77 | 3.21 | 7.24 |
| 28.27 | 3.16 | 2.98 |
| 28.91 | 3.09 | 10.74 |
| 29.18 | 3.06 | 7.70 |
| 30.39 | 2.94 | 12.58 |
| 31.04 | 2.88 | 7.39 |
| 32.42 | 2.76 | 7.07 |
| 33.44 | 2.68 | 2.63 |
| 34.03 | 2.63 | 3.54 |
| 36.13 | 2.49 | 1.61 |
| 36.85 | 2.44 | 2.20 |

Figure 9:
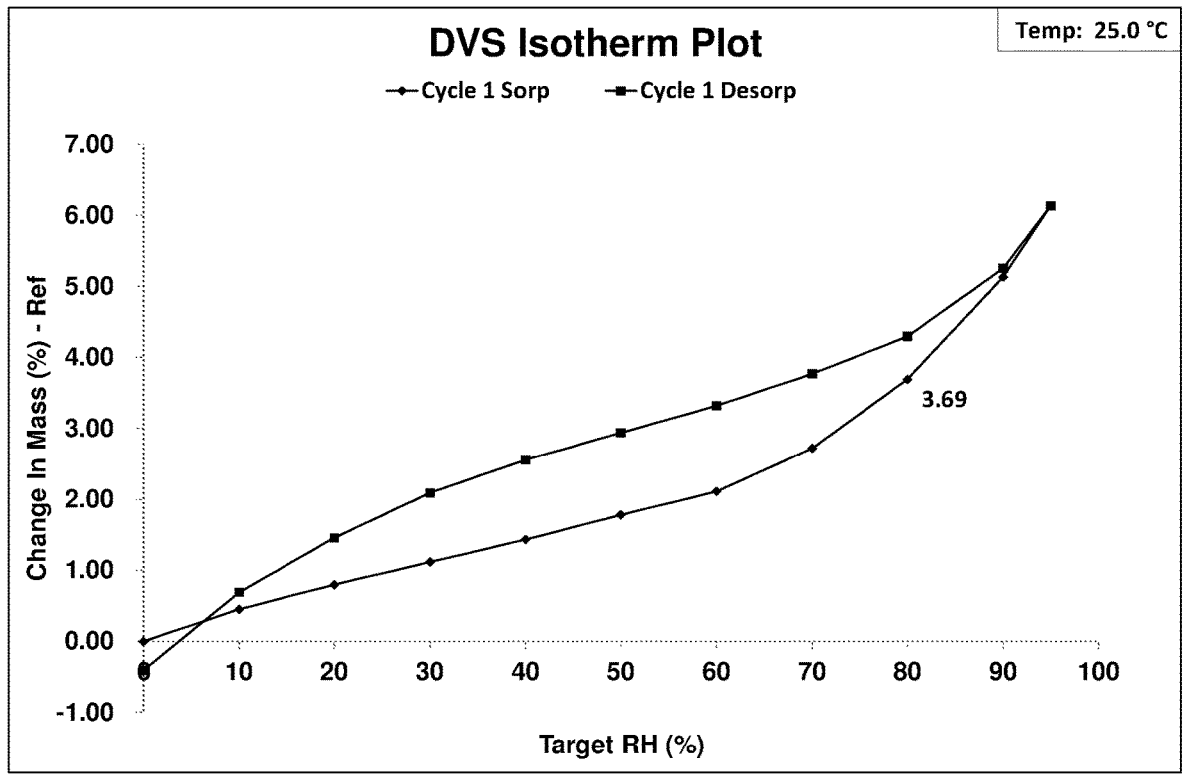
FIG. 9 shows a DVS plot of prior art amorphous.

Example 4: Preparation of Form CST 300.4 mg of Compound I solid was weighed into a glass vial, followed by the addition of 3.0 mL of methyl tert-butyl ether. After stirring at 50° C. for about 68 hours, a solid was isolated. After vacuum drying at 75° C. for 1 hour, the obtained solid is confirmed to be Form CSI of the present disclosure, and the XRPD data are shown in FIG. 9 and Table 4.

Figure 5:
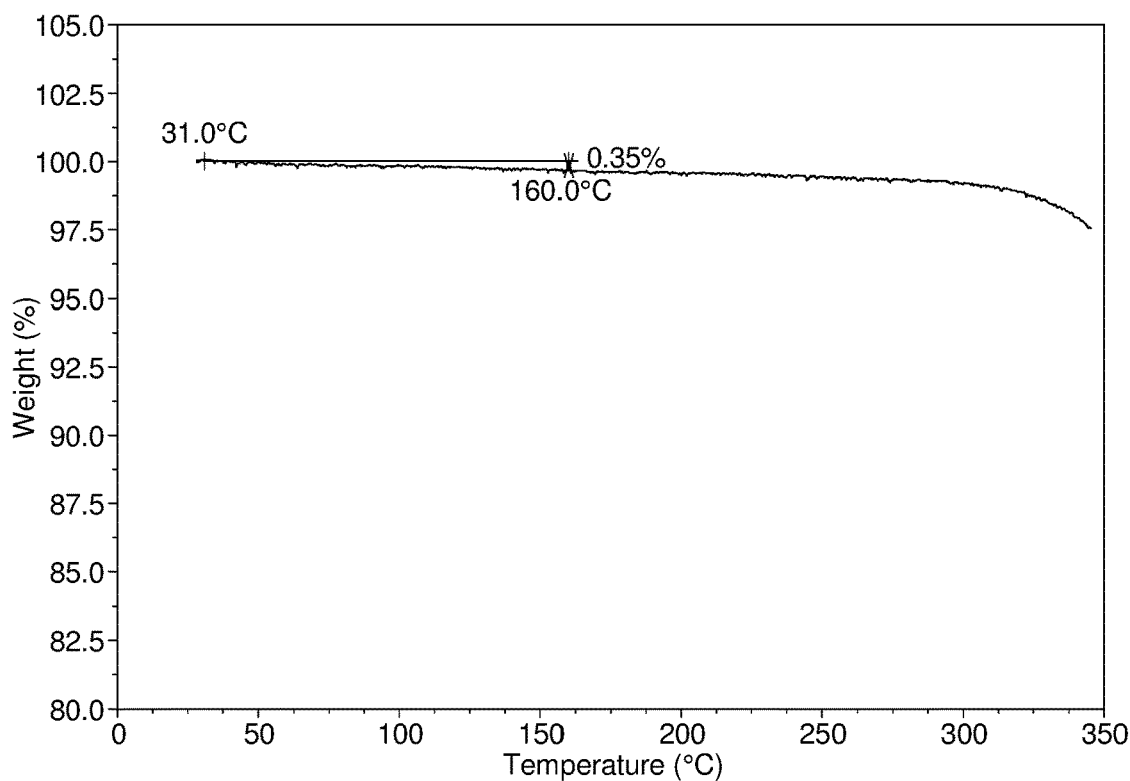
FIG. 5 shows a TGA curve of Form CSI.

The TGA curve is substantially as depicted in FIG. 5, which shows about 0.4% weight loss when heated from 31° C. to 160° C.

Figure 6:
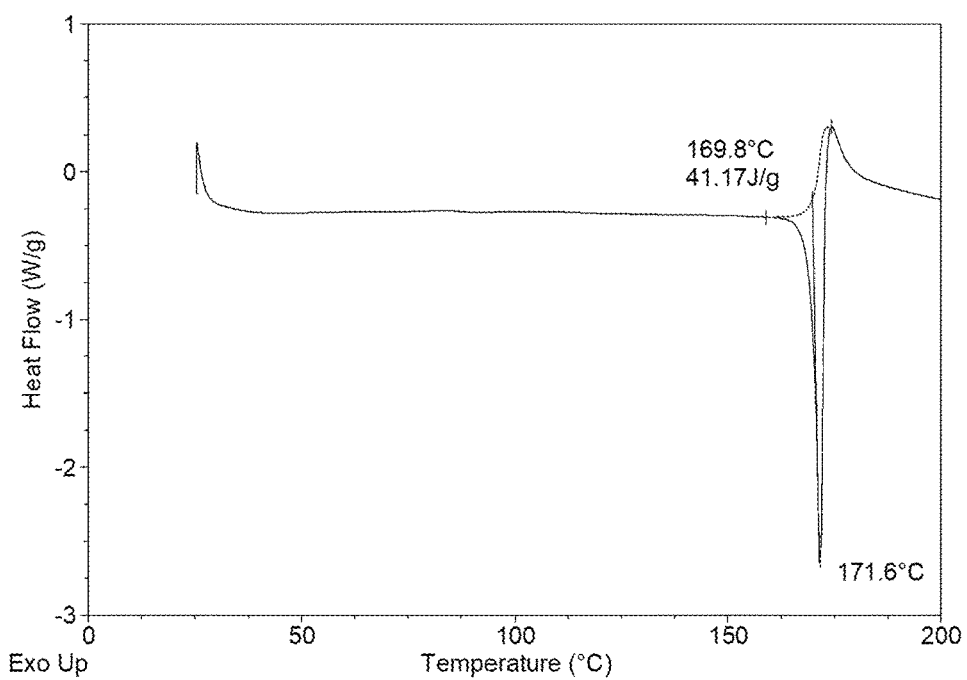
FIG. 6 shows a DSC curve of Form CSI.

The DSC curve is substantially as depicted in FIG. 6. It shows one endothermic peak at around 170° C. (onset temperature), which is the melting endothermic peak of Form CSI.

The $^1$H NMR data are as follows: $^1$HNMR (400 MHz, DMSO) δ (ppm) 7.75 (d, 1H), 7.52-7.36 (m, 4H), 7.21 (t, 1H), 7.14 (t, J=7.8 Hz, 4H), 6.98 (d, 1H), 6.91-6.76 (m, 1H), 6.13 (dd, J=16.5, 7.0 Hz, 1H), 5.69 (dd, J=16.7, 10.8 Hz, 1H), 4.82 (s, 2H), 4.50 (t, J=14.3 Hz, 1H), 4.15 (dd, J=33.9, 12.5 Hz, 2H), 3.76 (t, J=13.0 Hz, 0.5H), 3.16 (t, J=12.7 Hz, 0.5H), 2.79-2.61 (m, 0.5H), 2.45-2.29 (m, J=13.0, 9.1 Hz, 1H), 2.10-1.74 (m, 2H), 1.66-1.37 (m, 1H). (According to the structure of Compound I, the peak of one piperidine hydrogen appears at δ 3.33-3.76 ppm. Harf of this hydrogen is spitted and covered by the signal of water since it is close to the peak of water.)

TABLE 9

| 2θ (°) | d spacing (Å) | Relative intensity (%) |
|---|---|---|
| 7.67 | 11.53 | 36.95 |
| 7.88 | 11.22 | 10.54 |
| 10.07 | 8.78 | 6.04 |
| 10.56 | 8.38 | 6.47 |
| 11.00 | 8.04 | 54.02 |
| 12.03 | 7.36 | 45.91 |
| 13.21 | 6.70 | 15.50 |
| 13.63 | 6.50 | 32.17 |
| 14.02 | 6.32 | 14.97 |
| 15.06 | 5.88 | 6.22 |
| 15.49 | 5.72 | 11.71 |
| 16.08 | 5.51 | 35.68 |
| 17.33 | 5.12 | 2.04 |
| 18.47 | 4.80 | 42.70 |
| 18.73 | 4.74 | 43.49 |
| 19.26 | 4.61 | 6.38 |
| 20.11 | 4.42 | 22.02 |
| 20.85 | 4.26 | 9.97 |
| 21.34 | 4.16 | 15.95 |
| 21.65 | 4.11 | 12.00 |
| 22.32 | 3.98 | 7.77 |
| 22.79 | 3.90 | 100.00 |
| 23.68 | 3.76 | 24.11 |
| 24.18 | 3.68 | 8.70 |
| 24.46 | 3.64 | 11.52 |
| 24.82 | 3.59 | 23.38 |
| 26.30 | 3.39 | 9.10 |
| 27.49 | 3.25 | 5.45 |
| 27.79 | 3.21 | 6.74 |
| 28.90 | 3.09 | 6.79 |
| 30.38 | 2.94 | 11.72 |
| 31.14 | 2.87 | 2.74 |
| 32.42 | 2.76 | 7.51 |
| 34.13 | 2.63 | 3.52 |
| 36.12 | 2.49 | 1.82 |
| 36.90 | 2.44 | 2.04 |

Example 5: Physical and Chemical Stability of Form CSI

Figure 7:
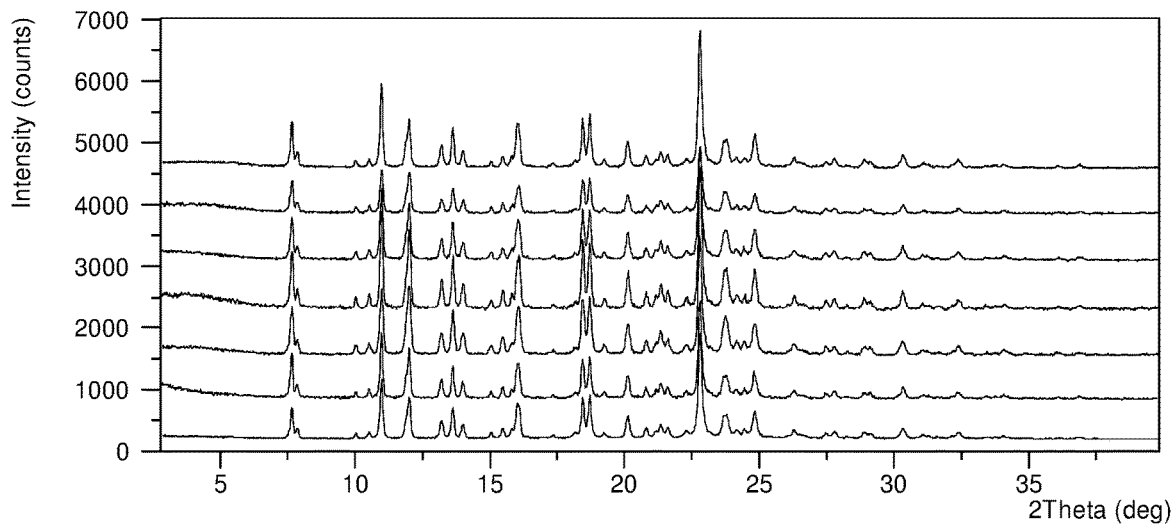
FIG. 7 shows an XRPD pattern overlay of Form CSI before and after storage (from top to bottom: initial, stored at 25° C./60% RH (open package) for 6 months, stored at 25° C./60% RH (sealed package) for 6 months, stored at 40° C./75% RH (open package) for 6 months, stored at 40° C./75% RH (sealed package) for 6 months, stored at 60° C./75% RH (open package) for 1 months, stored at 60° C./75% RH (sealed package) for 1 months).

A certain amount of Form CSI of the present disclosure and prior art amorphous were weighed and stored under 25° C./60% RH, 40° C./75% RH and 60° C./75% RH conditions, respectively. The purity and solid form were determined by UPLC and XRPD. The results are listed in Table 10, and the XRPD overlay of Form CSI before and after stability evaluation is shown in FIG. 7.

TABLE 10

| Initial solid form | Storage condition | Packing condition | Storage time | Solid form | Purity | Purity change | Impurity number exceed the qualificated threshold |
|---|---|---|---|---|---|---|---|
| Form CSI | Initial | N/A | N/A | Form CSI | 99.86% | N/A | 0 |
| | 25° C./60% RH | Sealed packaged | 6 months | Form CSI | 99.89% | 0.03% | 0 |
| | 25° C./60% RH | Open packaged | 6 months | Form CSI | 99.81% | −0.05% | 0 |
| | 40° C./75% RH | Sealed packaged | 6 months | Form CSI | 99.92% | 0.06% | 0 |
| | 40° C./75% RH | Open packaged | 6 months | Form CSI | 99.81% | −0.05% | 0 |
| | 60° C./75% RH | Sealed packaged | 1 month | Form CSI | 99.85% | −0.01% | 0 |
| | 60° C./75% RH | Open packaged | 1 month | Form CSI | 99.86% | 0.00% | 0 |
| Amorphous | Initial | N/A | N/A | Amorphous | 99.80% | N/A | 1 |
| | 25° C./60% RH | Sealed packaged | 6 months | Amorphous | 99.65% | −0.15% | 1 |
| | 25° C./60% RH | Open packaged | 6 months | Amorphous | 99.57% | −0.23% | 1 |
| | 40° C./75% RH | Sealed packaged | 6 months | Amorphous | 99.18% | −0.62% | 2 |
| | 40° C./75% RH | Open packaged | 6 months | Amorphous | 96.34% | −3.46% | 4 |
| | 60° C./75% RH | Sealed packaged | 1 month | Amorphous | 97.04% | −2.76% | 2 |
| | 60° C./75% RH | Open packaged | 1 month | Amorphous | 93.48% | −6.32% | 4 |

The dose of Compound I is 60 mg once daily.

The results show that Form CSI is stable for at least 6 months under 25° C./60% RH and 40° C./75% RH conditions, and the solid form and purity remain basically unchanged, indicating Form CSI has good stability under both long-term and accelerated conditions. After storage under 60° C./75% RH condition for 1 month, the solid form and purity remain basically unchanged, indicating Form CSI has good stability under stressed condition as well. The impurity content of Form CSI drug substance does not exceed the qualificated threshold throughout the stability investigation processes, which meets the requirements of pharmaceutical development. After storage at 25° C./60% RH, 40° C./75% RH and 60° C./75% RH, the purity of prior art amorphous decreased significantly, which is far below the requirements of pharmaceutical development. After storage at 40° C./75% RH for 6 months with open package, the purity decreased by 3.46%, and the number of impurities exceeding the qualificated threshold increased to four. After storage at 60° C./75% RH for only 1 month with sealed package, the purity decreased by 2.76%, and the number of impurities exceeding the qualificated threshold increased to two. After storage at 60° C./75% RH for only 1 month with open package, the purity decreased over 6.3%, and the number of impurities exceeding the qualificated threshold increased to four. The results indicate that Form CSI of the present disclosure has outstanding chemical stability when compared with prior art amorphous.

Example 6: Stability of Form CSI at High Temperature

Approximately 10 mg of Form CSI of the present disclosure and prior art amorphous were stored at 80° C. for 2 days, and the initial and final purities were determined by UPLC, as shown in Table 11.

TABLE 11

| Initial solid form | Package condition | Storage time | Initial purity | Final purity | Purity change |
|---|---|---|---|---|---|
| Form CSI | Glass vial with cap | 2 days | 99.94% | 99.95% | 0.01% |
| Amorphous | Glass vial with cap | 2 days | 99.80% | 98.64% | −1.16% |

The results indicate that the chemical purity of Form CSI basically remains unchanged for 2 days at 80° C., while significant degradation of amorphous is observed under the same condition. Form CSI of the present disclosure has superior stability at high temperature compared with the prior art amorphous.

Example 7: Hygroscopicity of Form CSI

Figure 8:
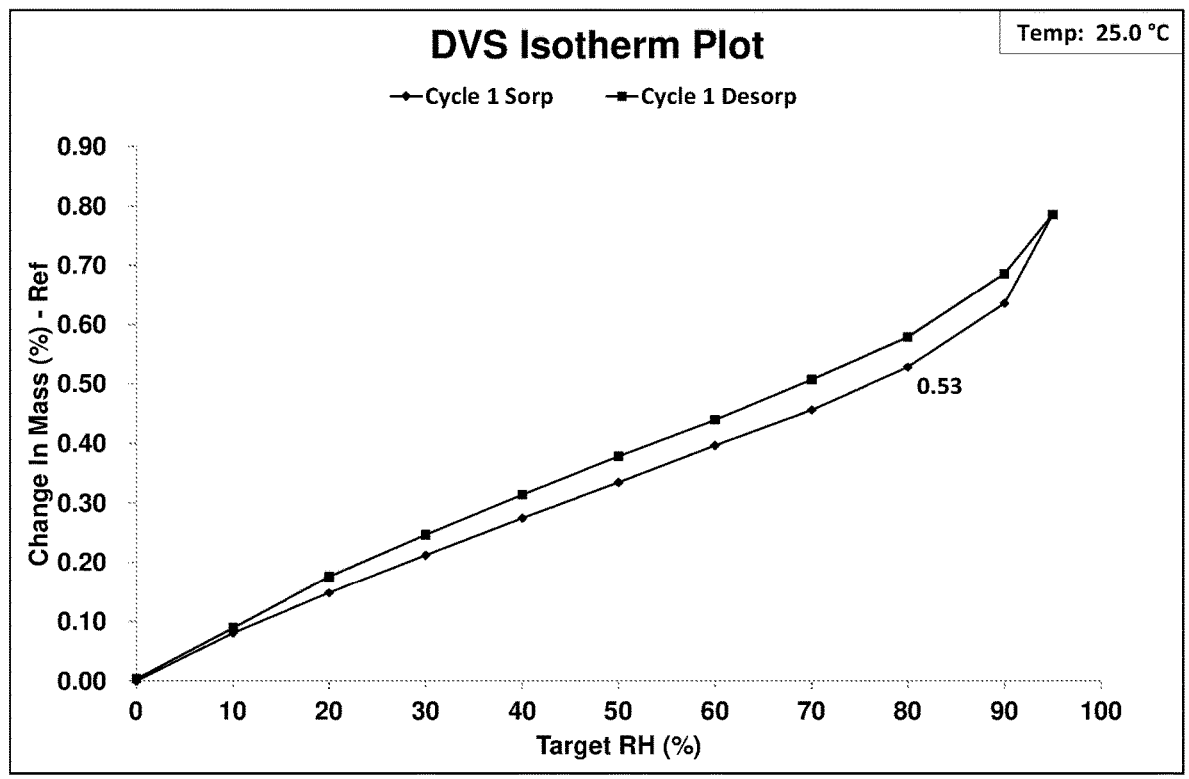
FIG. 8 shows a DVS plot of Form CSI.

Certain amounts of Form CSI of the present disclosure and prior art amorphous were sampled for hygroscopicity tests using dynamic vapor sorption (DVS) instrument. The weight change at each relative humidity is recorded during the cycle of 0% RH-95% RH-0% RH at 25° C., and the experimental results are listed in Table 12. The DVS plots of Form CSI and amorphous are as depicted in FIG. 8 and FIG. 9, respectively.

TABLE 12

| Form | Weight gain at 80% RH |
| --- | --- |
| Form CSI | 0.53% |
| Prior art solid | 3.69% |

The results show that Form CSI is slightly hygroscopic with a weight gain of 0.53% at 80% RH, while prior art solid is hygroscopic with a weight gain of 3.69% at 80% RH. The hygroscopicity of Form CSI is superior to that of prior art.

Description and definition of hygroscopicity (general notice 9103 drug hygroscopicity test guidelines in 2020 edition of Chinese Pharmacopoeia, experimental condition: 25±1° C., 80±2% RH):

Deliquescent: sufficient water is absorbed to form a liquid.

Very hygroscopic: increase in mass is equal to or greater than 15.0 percent.

Hygroscopic: increase in mass is less than 15.0 percent and equal to or greater than 2.0 percent.

Slightly hygroscopic: increase in mass is less than 2.0 percent and equal to or greater than 0.2 percent.

Non hygroscopic or almost non hygroscopic: increase in mass is less than 0.2 percent.

(The definition of hygroscopicity in the $10^{th}$ European Pharmacopoeia 5.11 is similar to the Chinese Pharmacopoeia.)

Example 8: Preparation of Form CSI Drug Product

Figure 10:
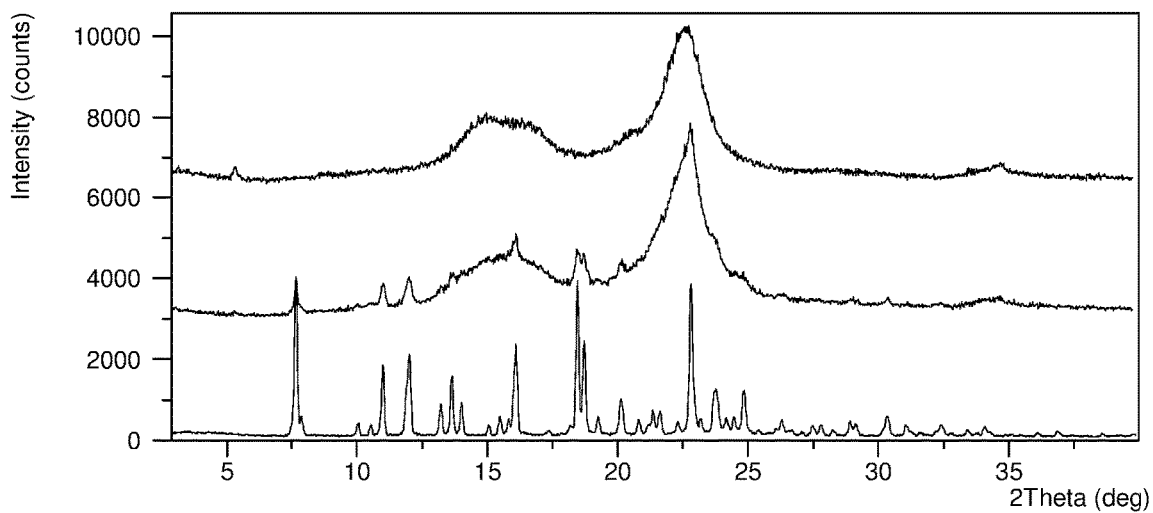
FIG. 10 shows an XRPD pattern overlay of Form CSI before and after formulation process (from top to bottom: excipients, after formulation process, and Form CSI).

According to the formulation and process in Table 13 and Table 14, the drug products were prepared with an appropriate amount of Form CSI of the present disclosure. XRPD were tested before and after formulation. The XRPD overlay is shown in FIG. 10, indicating Form CSI of the present disclosure is physically stable before and after the formulation process.

TABLE 13

| No. | Component | mg/unit | % (w/w) | Function |
| --- | --- | --- | --- | --- |
| 1 | Form CSI | 20 | 20 | API |
| 2 | Microcrystalline Cellulose | 69.5 | 69.5 | Fillers |
| 3 | Hydroxypropyl methyl cellulose | 3.0 | 3.0 | Adhesives |
| 4 | Crospovidone | 6.0 | 6.0 | Disintegrants |
| 5 | Colloidal silicon dioxide | 0.5 | 0.5 | Glidants |
| 6 | Magnesium stearate | 1.0 | 1.0 | Lubricants |
| Total | | 100.0 | 100.0 | / |

TABLE 14

| Stage | Procedure |
| --- | --- |
| Pre-blending | According to the formulation, No. 1-6 materials were weighed into a LDPE bag and blended for 2 minutes. |
| Simulation of dry granulation | The pre-mixed powders were tableted by the ENERPAC single punch manual tablet press equipped with a round die of φ 20 mm (tablet weight: 500 ± 100 mg; pressure: 5 ± 1 KN). The obtained tablets were pulverized and sieved through a 20-mesh sieve, and then the final mixed powders were obtained. |
| Tableting | The final mixed powders were tableted by the ENERPAC single punch manual tablet press equipped with a die of φ 9 * 4 mm (tablet weight: 100 ± 10 mg; pressure: 5 ± 1 KN). |
| Packing | one tablet of drug product and 1 g of desiccant were placed in a sealed 35 cc HDPE bottle. |

Example 9: The Stability of Form CSI Drug Product

Figure 11:
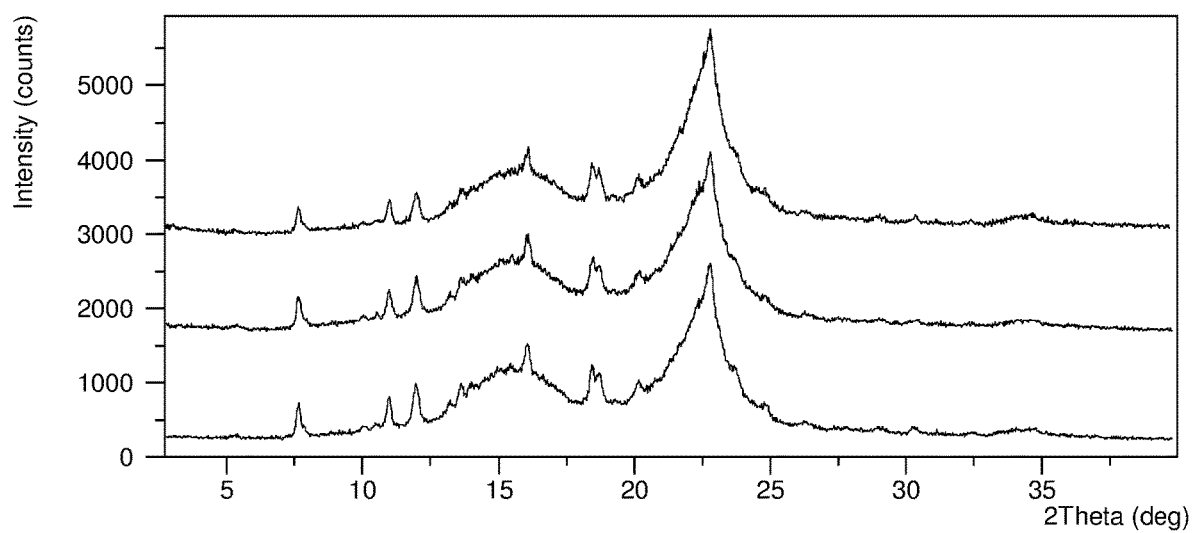
FIG. 11 shows an XRPD pattern overlay of Form CSI drug product stored under different conditions (from top to bottom: initial drug product, stored under 25° C./60% RH for 3 months, stored under 40° C./75% RH for 3 months).

To evaluate the stability of Form CSI in drug products, the packaged drug products prepared in Example 8 were stored under 25° C./60% RH and 40° C./75% RH conditions for 3 months, and the XRPD overlay of drug products before and after storage is as depicted in FIG. 11.

The results indicate that the drug products of Form CSI are stable under 25° C./60% RH and 40° C./75% RH conditions for at least 3 months.

The examples described above are only for illustrating the technical concepts and features of the present disclosure and are intended to make a person skilled in the art being able to understand the present disclosure. All these examples are not to limit the proception scope of the present disclosure. Any equivalent variations or modifications according to the spirit of the present disclosure should be covered by the protective scope of the present disclosure.

The invention claimed is:

1. A crystalline form of Compound I, wherein an X-ray powder diffraction pattern comprises characteristic peaks at 2theta values of 7.7°±0.2°, 11.0°±0.2°, 22.8°±0.2°, 12.0°±0.2°, 16.1°±0.2°, and 18.5°±0.2° using CuKα radiation

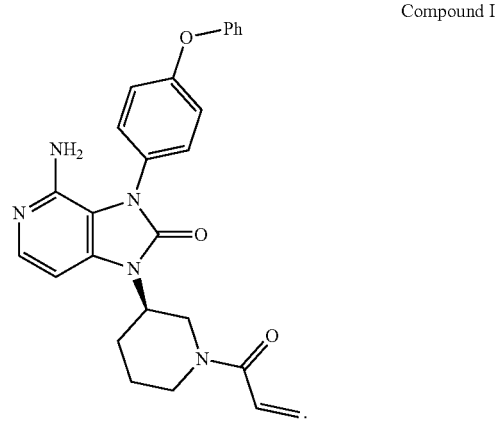 [SMILES: C=CC(=O)N1CCC[C@@H](n2c(=O)n(-c3ccc(Oc4ccccc4)cc3)c3c(N)nccc32)C1]

Compound I

2. The crystalline form of Compound I according to claim 1, wherein the X-ray powder diffraction pattern comprises at least one characteristic peak at 2theta values of 13.6°±0.2°, 20.1°±0.2°, and 24.8°±0.2° using CuKα radiation.

3. The crystalline form of Compound I according to claim 1, wherein the X-ray powder diffraction pattern is as depicted in FIG. 2 using CuKα radiation.

4. A pharmaceutical composition, wherein said pharmaceutical composition comprises a therapeutically effective amount of the crystalline form according to claim 1, and pharmaceutically acceptable excipients.

* * * * *